(12) United States Patent
Pandya et al.

(10) Patent No.: US 11,925,661 B2
(45) Date of Patent: *Mar. 12, 2024

(54) READY-TO-USE POTASSIUM PHOSPHATES IN SODIUM CHLORIDE SOLUTIONS

(71) Applicant: Nivagen Pharmaceuticals, Inc., Sacramento, CA (US)

(72) Inventors: Brijeshkumar B. Pandya, Sacramento, CA (US); Govind R. Jagadale, Sacramento, CA (US); Dasaradhi Lakkaraju, Sacramento, CA (US); Bala Tripura Sundari Chodavarapu, Davis, CA (US); Anand Shukla, Denver, CO (US); Jwalant Shukla, Sacramento, CA (US)

(73) Assignee: Nivagen Pharmaceuticals, Inc., Sacramento, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/460,941

(22) Filed: Sep. 5, 2023

(65) Prior Publication Data

US 2023/0405045 A1    Dec. 21, 2023

Related U.S. Application Data

(63) Continuation-in-part of application No. 17/499,001, filed on Oct. 12, 2021, now Pat. No. 11,813,291.

(60) Provisional application No. 63/090,518, filed on Oct. 12, 2020.

(51) Int. Cl.
| | | |
|---|---|---|
| *A61K 33/42* | (2006.01) | |
| *A61J 1/10* | (2006.01) | |
| *A61K 9/08* | (2006.01) | |
| *A61M 5/168* | (2006.01) | |
| *A61M 39/02* | (2006.01) | |

(52) U.S. Cl.
CPC ............ *A61K 33/42* (2013.01); *A61J 1/10* (2013.01); *A61K 9/08* (2013.01)

(58) Field of Classification Search
None
See application file for complete search history.

(56) References Cited

U.S. PATENT DOCUMENTS

| | | |
|---|---|---|
| 10,342,813 B2 | 7/2019 | Pizza |
| 10,632,150 B1 | 4/2020 | Thomas et al. |
| 11,141,430 B1 | 10/2021 | Koneru et al. |
| 2014/0364503 A1 | 12/2014 | Owoo et al. |

FOREIGN PATENT DOCUMENTS

CN    106265499 A    1/2017

*Primary Examiner* — Danah Al-Awadi
(74) *Attorney, Agent, or Firm* — Umberg Zipser LLP

(57) ABSTRACT

Ready-to-use (RTU) potassium phosphates solutions for phosphorus replacement therapy are presented that include potassium phosphate and sodium chloride at a fixed volume with 1.5 to 15 mmol/100 mL phosphorus, no more than 22 mEq/100 mL potassium and less than 50 mcg/L aluminum.

20 Claims, 27 Drawing Sheets

800 mL of Water in SS316 container.

↓

Add Potassium phosphate dibasic into 800 mL water, stir for 10 minute or until dissolve with 2000 RPM continuously.

↓

Add Potassium phosphate monobasic into 800 mL water, stir for 10 minute or until dissolve with 2000 RPM continuously.

↓

Add Sodium Chloride into 800 mL water, stir for 10 minute or until dissolve with 2000 RPM continuously.

↓

Q.S. with final volume of water and filter through 0.45μm PVDF filter.

↓

Filter with in-line 0.22μm PVDF filter and fill the liquid in 100 ml 1T Port IV bag (Ready to Use) and seal it (Consider as Aseptic technique).

↓

Or adopt Terminal Sterilization technique for the product sterility.

↓

Pack into Aluminum pouches and seal it under nitrogen environment.

↓

Potassium Phosphates in Sodium Chloride Injection, RTU

*FIG.3*

B. No.#PQ32052
Autoclave @ 121°C for 15 Minutes
TechnoFlex 1T PP Bag + Al Pouch

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.551 | 6.61 | 6.56 | 6.62 | 6.56 | 6.57 | Not Analyzed (Sample sent to Sanuova for Al content development at 3 month) |
| Osmolality (mOsm/kg) | | 576 | 569 | 565 | 606 | 592 | 583 | 595 | |
| LPC | 10µm | 227 | 553 | 113 | 427 | 80 | 233 | 187 | |
| | 25µm | 20 | 13 | 7 | 13 | 13 | 7 | 0 | |
| Assay of Anions | % Phosphorus | 101.0 | 101.0 | 98.0 | 99.1 | 94.4 | 101.6 | 99.5 | |
| | % Chloride | 102.0 | 101.8 | 96.7 | 101.2 | 92.5 | 102.3 | 99.1 | |
| Assay of Cations | % Potassium | 102.2 | 102.0 | 98.6 | 98.3 | 94.3 | 101.7 | 98.6 | |
| | % Sodium | 99.8 | 99.7 | 99.2 | 100.3 | 92.8 | 101.6 | 98.5 | |

TechnoFlex 1T PP Bag (Without Al Pouches)

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.551 | 6.58 | 6.58 | 6.57 | 6.56 | 6.54 | 6.54 |
| Osmolality (mOsm/kg) | | 576 | 569 | 571 | 608 | 622 | 578 | 560 | 615 |
| LPC | 10µm | 227 | 553 | 227 | 440 | 940 | 140 | 407 | 280 |
| | 25µm | 20 | 13 | 20 | 7 | 20 | 0 | 27 | 13 |
| Assay of Anions | % Phosphorus | 101.0 | 101.0 | 99.3 | 100.5 | 101.0 | 101.7 | 101.4 | 110.2 |
| | % Chloride | 102.0 | 101.8 | 98.4 | 99.0 | 8.0 | 99.8 | 100.4 | 108.0 |
| Assay of Cations | % Potassium | 102.2 | 102.0 | 100.5 | 99.6 | 100.3 | 99.9 | 99.8 | 108.0 |
| | % Sodium | 99.8 | 99.7 | 100.9 | 98.5 | 102.7 | 99.7 | 99.7 | 107.7 |

* CCS- A Clear colorless solution, free from visible foreign particles

FIG.9

Autoclave @ 121°C for 15 Minutes

Grifols 1T PP Bag + Al Pouch

| Test | | Bulk Solution | Initial | 3M 25/40 | 3M 30/65 | 3M 40/15 | 6M 25/40 | 6M 30/65 | 6M 40/15 |
|---|---|---|---|---|---|---|---|---|---|
| Assay of Anions | % Phosphorus | 101.0 | 100.9 | 98.8 | 98.8 | 95.0 | 100.3 | 100.0 | 100.3 |
| | % Chloride | 102.0 | 101.9 | 98.4 | 97.7 | 94.6 | 99.3 | 99.0 | 98.6 |
| Assay of Cations | % Potassium | 102.2 | 101.8 | 99.9 | 98.1 | 96.0 | 99.7 | 98.7 | 98.6 |
| | % Sodium | 99.8 | 99.4 | 100.9 | 96.9 | 94.6 | 99.2 | 98.6 | 98.2 |

Grifols 1T PP Bag (Without Al Pouches)

| Test | | Bulk Solution | Initial | 3M 25/40 | 3M 30/65 | 3M 40/15 | 6M 25/40 | 6M 30/65 | 6M 40/15 |
|---|---|---|---|---|---|---|---|---|---|
| Description* | | CCS | CCS | CCS | CCS | CCS | CCS | CCS | CCS |
| pH of Solution | | 6.543 | 6.548 | 6.62 | 6.36 | 6.58 | 6.39 | 6.56 | 6.56 |
| Osmolality (mOsm/kg) | | 576 | 579 | 574 | 604 | 626 | 581 | 591 | 628 |
| LPC | 10µm | 227 | 187 | 107 | 60 | 587 | 192 | 173 | 107 |
| | 25µm | 20 | 0 | 7 | 0 | 27 | 7 | 33 | 33 |
| Assay of Anions | % Phosphorus | 101.0 | 100.9 | 99.5 | 100.8 | 102.0 | 102.8 | 102.1 | 111.8 |
| | % Chloride | 102.0 | 101.9 | 99.2 | 99.0 | 100.5 | 100.6 | 101.0 | 109.7 |
| Assay of Cations | % Potassium | 102.2 | 101.8 | 101.2 | 99.7 | 102.9 | 100.4 | 100.7 | 109.6 |
| | % Sodium | 99.8 | 99.4 | 101.8 | 98.7 | 101.3 | 99.8 | 100.4 | 109.3 |

* CCS- A Clear colorless solution, free from visible foreign particles

*FIG.9 cont'd*

Autoclave @ 121°C for 15 Minutes

TechnoFlex 2T PP Bag + Al Pouch

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.549 | 6.61 | 6.63 | 6.58 | 6.54 | 6.57 | 6.58 |
| Osmolality (mOsm/kg) | | 576 | 570 | 568 | 601 | 569 | 577 | 577 | 572 |
| LPC | 10μm | 227 | 287 | 360 | 893 | 183 | 520 | 180 | 100 |
| | 25μm | 20 | 27 | 30 | 33 | 20 | 47 | 27 | 13 |
| Assay of Anions | % Phosphorus | 101.0 | 101.6 | 98.5 | 98.4 | 97.9 | 100.3 | 98.7 | 100.5 |
| | % Chloride | 102.0 | 102.6 | 97.7 | 97.5 | 96.2 | 99.4 | 97.7 | 98.6 |
| Assay of Cations | % Potassium | 102.2 | 102.5 | 99.7 | 97.7 | 99.3 | 99.5 | 97.4 | 98.9 |
| | % Sodium | 99.8 | 100.1 | 100.2 | 96.7 | 96.6 | 99.0 | 97.3 | 98.6 |

TechnoFlex 2T PP Bag (Without Al Pouches)

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.549 | 6.63 | 6.58 | 6.6 | 6.57 | 6.57 | 6.55 |
| Osmolality (mOsm/kg) | | 576 | 570 | 573 | 604 | 620 | 584 | 583 | 615 |
| LPC | 10μm | 227 | 287 | 133 | 353 | 1867 | 167 | 240 | 460 |
| | 25μm | 20 | 27 | 7 | 7 | 20 | 0 | 7 | 13 |
| Assay of Anions | % Phosphorus | 101.0 | 101.6 | 98.8 | 100.1 | 103.0 | 109.2 | 102.5 | 109.5 |
| | % Chloride | 102.0 | 102.6 | 98.2 | 99.2 | 102.1 | 112.4 | 101.0 | 107.4 |
| Assay of Cations | % Potassium | 102.2 | 102.5 | 100.6 | 99.4 | 104.1 | 100.4 | 100.7 | 107.3 |
| | % Sodium | 99.8 | 100.1 | 101.1 | 98.5 | 102.3 | 100.0 | 100.5 | 107.0 |

* CCS- A Clear colorless solution, free from visible foreign particles

FIG.9 cont'd

Autoclave @ 121°C for 15 Minutes

Bausch 2T PP Bag + Al Pouch

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.555 | 6.63 | 6.62 | 6.59 | 6.55 | 6.58 | 6.58 |
| Osmolality (mOsm/kg) | | 576 | 572 | 567 | 599 | 591 | 582 | 580 | 581 |
| LPC | 10µm | 227 | 153 | 127 | 427 | 240 | 153 | 240 | 333 |
| | 25µm | 20 | 13 | 13 | 20 | 0 | 7 | 7 | 7 |
| Assay of Anions | % Phosphorus | 101.0 | 101.6 | 98.0 | 98.9 | 96.8 | 101.2 | 100.0 | 100.8 |
| | % Chloride | 102.0 | 102.6 | 97.7 | 102.6 | 95.9 | 99.3 | 98.8 | 99.2 |
| Assay of Cations | % Potassium | 102.2 | 102.4 | 99.6 | 98.8 | 103.2 | 99.7 | 98.7 | 99.3 |
| | % Sodium | 99.8 | 100.2 | 100.3 | 102.0 | 96.3 | 99.0 | 98.5 | 99.0 |

Bausch 2T PP Bag (Without Al Pouches)

| Test | | Bulk Solution | Initial | Condition | | | | | |
|---|---|---|---|---|---|---|---|---|---|
| | | | | 3M 25/40 | 3M 30/65 | 3M 40/15 | 6M 25/40 | 6M 30/65 | 6M 40/15 |
| Description* | | CCS | CCS | CCS | CCS | CCS | CCS | CCS | CCS |
| pH of Solution | | 6.543 | 6.555 | 6.62 | 6.56 | 6.62 | 6.59 | 6.56 | 6.56 |
| Osmolality (mOsm/kg) | | 576 | 572 | 571 | 610 | 625 | 578 | 593 | 618 |
| LPC | 10µm | 227 | 153 | 193 | 93 | 40 | 127 | 247 | 240 |
| | 25µm | 20 | 13 | 0 | 0 | 0 | 0 | 0 | 20 |
| Assay of Anions | % Phosphorus | 101.0 | 101.6 | 96.8 | 99.5 | 102.1 | 104.2 | 102.3 | 109.7 |
| | % Chloride | 102.0 | 102.6 | 96.2 | 98.8 | 100.8 | 104.1 | 100.6 | 108.0 |
| Assay of Cations | % Potassium | 102.2 | 102.4 | 98.6 | 98.7 | 103.1 | 100.7 | 100.0 | 107.7 |
| | % Sodium | 99.8 | 100.2 | 99.1 | 98.1 | 102.1 | 100.5 | 99.9 | 107.2 |

* CCS: A Clear colorless solution, free from visible foreign particles

*FIG.9 cont'd*

Autoclave @ 121°C for 15 Minutes

TechnoFlex 2T PVC Bag + Al Pouch

| Test | | Bulk Solution | Initial | 3M 25/40 | 3M 30/65 | 3M 40/15 | 6M 25/40 | 6M 30/65 | 6M 40/15 |
|---|---|---|---|---|---|---|---|---|---|
| Description* | | CCS | CCS | CCS | CCS | CCS | CCS | CCS | CCS |
| pH of Solution | | 6.543 | 6.550 | 6.61 | 6.57 | 6.57 | 6.57 | 6.57 | 6.56 |
| Osmolality (mOsm/kg) | | 576 | 573 | 573 | 606 | 606 | 594 | 589 | 581 |
| LPC | 10µm | 227 | 153 | 267 | 600 | 360 | 313 | 193 | 87 |
| | 25µm | 20 | 13 | 13 | 33 | 7 | 0 | 7 | 7 |
| Assay of Anions | % Phosphorus | 101.0 | 101.9 | 99.4 | 99.7 | 100.5 | 102.6 | 101.3 | 102.9 |
| | % Chloride | 102.0 | 103.1 | 98.8 | 98.8 | 99.4 | 101.1 | 100.5 | 101.2 |
| Assay of Cations | % Potassium | 102.2 | 102.3 | 100.7 | 999.1 | 101.6 | 102.1 | 99.7 | 101.3 |
| | % Sodium | 99.8 | 100.1 | 101.3 | 98.2 | 99.8 | 100.7 | 99.6 | 100.9 |

TechnoFlex 2T PVC Bag (Without Al Pouches)

| Test | | Bulk Solution | Initial | 3M 25/40 | 3M 30/65 | 3M 40/15 | 6M 25/40 | 6M 30/65 | 6M 40/15 |
|---|---|---|---|---|---|---|---|---|---|
| Description* | | CCS | CCS | CCS | CCS | CCS | CCS | CCS | CCS |
| pH of Solution | | 6.543 | 6.550 | 6.61 | 6.6 | 6.6 | 6.55 | 6.55 | 6.45 |
| Osmolality (mOsm/kg) | | 576 | 573 | 607 | 657 | 646 | 636 | 649 | 1092 |
| LPC | 10µm | 227 | 153 | 320 | 253 | 147 | 933 | 260 | 161 |
| | 25µm | 20 | 13 | 20 | 13 | 27 | 7 | 13 | 7 |
| Assay of Anions | % Phosphorus | 101.0 | 101.9 | 104.7 | 110.4 | 142.7 | 123.2 | 113.7 | 224.2 |
| | % Chloride | 102.0 | 103.1 | 104.4 | 109.8 | 141.5 | 116.1 | 112.3 | 222.7 |
| Assay of Cations | % Potassium | 102.2 | 102.3 | 107.1 | 110.1 | 145.3 | 112.7 | 111.9 | 218.7 |
| | % Sodium | 99.8 | 100.1 | 107.6 | 109.4 | 142.4 | 112.3 | 111.7 | 217.7 |

* CCS - A Clear colorless solution, free from visible foreign particles

Autoclave @ 121°C for 15 Minutes

TechnoFlex II PP Bag + Al Pouch

| Test | | Bulk Solution | Initial | 1M 2-8 | 1M 25/40 | 1M 30/65 | 1M 40/15 | 6M 2-8 | 6M 25/40 | 6M 30/65 | 6M 40/15 |
|---|---|---|---|---|---|---|---|---|---|---|---|
| Description* | | CCS | CCS | CCS | CCS | CCS | CCS | CCS | CCS | CCS | CCS |
| pH of Solution | | 6.61 | 6.58 | 6.59 | 6.61 | 6.62 | 6.56 | 6.67 | 6.66 | 6.67 | 6.69 |
| Osmolality (mOsm/kg) | | 574 | 569 | 577 | 580 | 577 | 581 | 573 | 575 | 578 | 575 |
| LPC | 10µm | 273 | 240 | 213 | 180 | 500 | 807 | 487 | 433 | 327 | 347 |
| | 25µm | 27 | 7 | 7 | 0 | 20 | 20 | 20 | 53 | 7 | 13 |
| Assay of Anions | % Phosphorus | 100.8 | 100.8 | 98.9 | 97.7 | 98.3 | 98.1 | 99.8 | 99.9 | 103.2 | 101.4 |
| | % Chloride | 99.0 | 105.4 | 96.1 | 94.8 | 98.1 | 95.0 | 100.7 | 101.5 | 103.8 | 100.7 |
| Assay of Cations | % Potassium | 101.1 | 99.4 | 98.8 | 97.4 | 98.7 | 98.0 | 101.1 | 100.6 | 101.5 | 101.7 |
| | % Sodium | 101.5 | 98.1 | 98.3 | 96.8 | 98.7 | 97.3 | 100.3 | 99.8 | 102.2 | 100.8 |

* CCS - A Clear colorless solution, free from visible foreign particles

Autoclave @ 121°C for 15 Minutes

Grifols II PP Bag + Al Pouch

| Test | | Bulk Solution | Initial | 1M 2-8 | 1M 25/40 | 1M 30/65 | 1M 40/15 | 6M 2-8 | 6M 25/40 | 6M 30/65 | 6M 40/15 |
|---|---|---|---|---|---|---|---|---|---|---|---|
| Description* | | CCS | CCS | CCS | CCS | CCS | CCS | CCS | CCS | CCS | CCS |
| pH of Solution | | 6.61 | 6.55 | 6.53 | 6.57 | 6.59 | 6.60 | 6.69 | 6.69 | 6.67 | 6.70 |
| Osmolality (mOsm/kg) | | 574 | 572 | 579 | 575 | 576 | 581 | 572 | 573 | 571 | 573 |
| LPC | 10µm | 273 | 153 | 387 | 1573 | 527 | 333 | 273 | 287 | 473 | 189 |
| | 25µm | 27 | 7 | 20 | 93 | 53 | 93 | 33 | 27 | 67 | 27 |
| Assay of Anions | % Phosphorus | 100.8 | 101.5 | 97.3 | 98.3 | 98.9 | 97.3 | 100.7 | 100.9 | 100.3 | 101.2 |
| | % Chloride | 99.0 | 106.4 | 94.2 | 95.1 | 95.5 | 94.6 | 101.1 | 103.3 | 103.2 | 102.1 |
| Assay of Cations | % Potassium | 101.1 | 100.2 | 97.1 | 98.5 | 98.7 | 97.7 | 100.6 | 100.7 | 100.4 | 100.7 |
| | % Sodium | 101.5 | 98.9 | 96.8 | 98.0 | 98.2 | 97.4 | 99.9 | 99.8 | 99.7 | 99.9 |

* CCS - A Clear colorless solution, free from visible foreign particles

Aseptic Filling

TechnoFlex 1T PP Bag + Al Pouch

| Test | | Bulk Solution | Bulk_1M 2-8 | Bulk_1M 40/15 | Bulk_6M 2-8 | Bulk_6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.53 | | | | | 6.6 | 6.59 | 6.52 | 6.59 | 6.5 | 6.6 | 6.66 | 6.65 | 6.7 | 6.68 |
| Osmolality (mOsm/kg) | | 580 | | Not Applicable | | | 581 | 568 | 568 | 571 | 460 | 570 | 573 | 568 | 571 | 569 |
| LPC | 10µm | Not Applicable | | | | | 487 | 27 | 93 | 127 | 460 | 327 | 670 | 760 | 387 | 367 |
| | 25µm | | | | | | 0 | 7 | 13 | 7 | 40 | 7 | 13 | 20 | 33 | 7 |
| Assay of Anions | % Phosphorus | 97.3 | 101.4 | 103.2 | 101.5 | 115.9 | 98.0 | 100.2 | 99.9 | 100.5 | 102.5 | 100.9 | 103.3 | 103.4 | 102.7 | 102.3 |
| | % Chloride | 96.5 | 99.4 | 101.7 | 100.2 | 115.0 | 97.1 | 98.2 | 98.3 | 100.4 | 104.0 | 101.9 | 102.2 | 102.0 | 101.4 | 101.3 |
| Assay of Cations | % Potassium | 102.1 | 100.9 | 103.5 | 99.1 | 102.0 | 102.4 | 100.9 | 100.6 | 102.3 | 101.5 | 99.6 | 100.2 | 100.1 | 100.0 | 101.0 |
| | % Sodium | 101.1 | 101.2 | 101.9 | 98.8 | 101.3 | 101.3 | 101.6 | 101.1 | 98.7 | 98.7 | 95.3 | 100.1 | 100.2 | 99.7 | 100.1 |

* CCS: A Clear colorless solution, free from visible foreign particles

Autoclave @ 121°C for 15 Minutes (Autoclave Pressure: Max-3.18 bar, Min-3.00 bar)

Infanref (Pekytra APP1148) 1T PP Bag + Al Pouch

| Test | | Bulk Solution | Bulk_1M 2-8 | Bulk_1M 40/15 | Bulk_6M 2-8 | Bulk_6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.58 | 6.55 | 6.59 | 6.58 | 6.59 | 6.52 | 6.69 | 6.66 | 6.69 | 6.64 |
| Osmolality (mOsm/kg) | | 580 | | Not Applicable | | | 585 | 581 | 574 | 580 | 567 | 573 | 574 | 571 | 570 | 570 |
| LPC | 10µm | Not Applicable | | | | | 247 | 220 | 67 | 33 | 267 | 173 | 293 | 733 | 107 | 1040 |
| | 25µm | | | | | | 13 | 0 | 0 | 0 | 47 | 13 | 13 | 30 | 0 | 7 |
| Assay of Anions | % Phosphorus | 97.1 | 101.4 | 103.2 | 103.5 | 115.9 | 99.6 | 100.2 | 99.1 | 100.9 | 100.6 | 103.1 | 103.6 | 103.5 | 103.0 | 102.7 |
| | % Chloride | 96.5 | 99.4 | 101.7 | 100.2 | 115.0 | 97.2 | 98.1 | 97.2 | 100.7 | 102.1 | 102.3 | 101.4 | 102.9 | 103.4 | 103.4 |
| Assay of Cations | % Potassium | 102.1 | 100.9 | 103.5 | 99.1 | 102.0 | 101.1 | 100.3 | 99.7 | 100.6 | 99.8 | 102.5 | 100.6 | 101.3 | 100.6 | 101.1 |
| | % Sodium | 101.1 | 101.2 | 101.9 | 98.8 | 101.3 | 101.6 | 101.0 | 100.3 | 100.7 | 100.3 | 102.4 | 100.1 | 101.2 | 100.3 | 100.9 |

* CCS: A Clear colorless solution, free from visible foreign particles

Autoclave @ 121°C for 15 Minutes (Autoclave Pressure: Max-3.18 bar, Min-2.98 bar)
BioxoPharm (A1312A) 1T PP Bag + Al Pouch

| Test | | Bulk Solution | Bulk 1M 2-8 | Bulk 1M 40/15 | Bulk 6M 2-8 | Bulk 6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.60 | 6.59 | 6.59 | 6.58 | 6.59 | 6.59 | 6.7 | 6.64 | 6.67 | 6.68 |
| Osmolality (mOsm/kg) | | 580 | Not Applicable | | | | 585 | 583 | 582 | 577 | 574 | 575 | 578 | 572 | 567 | 568 |
| LPC | 10μm | Not Applicable | | | | | 987 | 360 | 113 | 1397 | 2440 | 537 | 487 | 2033 | 387 | 106 |
| | 25μm | | | | | | 20 | 0 | 7 | 180 | 53 | 40 | 47 | 11 | 0 | 20 |
| Assay of Anions | % Phosphorus | 97.3 | 101.4 | 103.2 | | 103.9 | 97.4 | 99.6 | 99.3 | 101.3 | 102.0 | 101.8 | 102.7 | 103.8 | 103.8 | 103.2 |
| | % Chloride | 96.5 | 99.4 | 101.7 | 101.5 | 103.0 | 96.8 | 97.3 | 97.5 | 103.6 | 103.4 | 103.5 | 102.0 | 103.1 | 102.7 | 103.6 |
| Assay of Cations | % Potassium | 102.1 | 100.9 | 103.5 | 99.1 | 102.9 | 102.3 | 99.8 | 100.2 | 101.5 | 101.0 | 99.9 | 101.0 | 101.9 | 101.5 | 103.1 |
| | % Sodium | 101.1 | 101.2 | 103.9 | 99.8 | 101.8 | 101.3 | 100.3 | 100.8 | 102.1 | 101.5 | 100.3 | 100.7 | 101.3 | 100.9 | 102.3 |

* CCS- A Clear colorless solution, free from visible foreign particles

Autoclave @ 121°C for 5 Minutes (Autoclave Pressure: Max-3.19 bar, Min-2.98 bar)
TechnoFlex 1T PP Bag + Al Pouch

| Test | | Bulk Solution | Bulk 1M 2-8 | Bulk 1M 40/15 | Bulk 6M 2-8 | Bulk 6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.60 | 6.55 | 6.59 | 6.59 | 6.6 | 6.6 | 6.64 | 6.66 | 6.69 | 6.64 |
| Osmolality (mOsm/kg) | | 580 | Not Applicable | | | | 587 | 581 | 586 | 569 | 568 | 567 | 575 | 570 | 569 | 576 |
| LPC | 10μm | Not Applicable | | | | | 346 | 46 | 60 | 469 | 906 | 287 | 59 | 173 | 127 | 207 |
| | 25μm | | | | | | 13 | 7 | 13 | 20 | 27 | 40 | 7 | 0 | 7 | 7 |
| Assay of Anions | % Phosphorus | 97.3 | 101.4 | 103.2 | | 103.9 | 98.1 | 99.5 | 99.3 | 101.2 | 101.6 | 102.3 | 102.5 | 101.6 | 102.6 | 102.3 |
| | % Chloride | 96.5 | 99.4 | 101.7 | 100.2 | 103.0 | 96.9 | 97.6 | 97.6 | 101.7 | 101.6 | 101.6 | 101.8 | 102.2 | 101.7 | 101.3 |
| Assay of Cations | % Potassium | 102.1 | 100.9 | 103.5 | 99.1 | 102.9 | 102.3 | 100.4 | 100.4 | 101.1 | 101.2 | 100.9 | 100.7 | 101.1 | 100.7 | 101.0 |
| | % Sodium | 101.1 | 101.2 | 103.9 | 98.8 | 101.8 | 101.5 | 100.9 | 101.1 | 96.7 | 99.7 | 98.5 | 100.2 | 100.6 | 100.2 | 100.6 |

* CCS- A Clear colorless solution, free from visible foreign particles

Autoclave @ 115°C for 28 Minutes (Autoclave Pressure: Max 2.61 bar, Min 2.45 bar)

Infusomat (Polycine APP3145); 1T PP Bag + Al Pouch

| Test | | Bulk Solution | Bulk_1M 2-8 | Bulk_1M 40/15 | Bulk_6M 2-8 | Bulk_6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.61 | 6.49 | 6.52 | 6.58 | 6.58 | 6.58 | 6.56 | 6.58 | 6.57 | 6.58 |
| Osmolality (mOsm/kg) | | 586 | Not Applicable | | | | 574 | 568 | 569 | 571 | 572 | 572 | 572 | 572 | 570 | 568 |
| LPC | 10μm | Not Applicable | | | | | 1736 | 60 | 333 | 2553 | 1167 | 387 | 73 | 487 | 620 | 120 |
| | 25μm | | | | | | 13 | 0 | 100 | 107 | 53 | 20 | 7 | 27 | 33 | 0 |
| Assay of Anions | % Phosphorus | 97.3 | 101.4 | 103.2 | 101.5 | 115.9 | 99.4 | 101.0 | 101.6 | 102.5 | 101.1 | 101.1 | 102.1 | 103.1 | 102.5 | 103.3 |
| | % Chloride | 96.5 | 99.4 | 101.7 | 100.2 | 115.0 | 97.2 | 98.5 | 98.5 | 102.2 | 102.6 | 102.8 | 101.5 | 101.5 | 101.9 | 101.3 |
| Assay of Cations | % Potassium | 102.1 | 100.9 | 103.5 | 99.1 | 112.0 | 102.9 | 99.6 | 100.0 | 101.1 | 101.1 | 101.6 | 100.2 | 100.1 | 99.6 | 100.5 |
| | % Sodium | 101.1 | 101.2 | 103.9 | 98.8 | 111.8 | 101.3 | 100.3 | 100.6 | 100.3 | 100.4 | 101.2 | 100.1 | 100.2 | 100.3 | 100.9 |

*CCS- A Clear colorless solution, free from visible foreign particles

Autoclave @ 115°C for 28 Minutes (Autoclave Pressure: Max 2.61 bar, Min 2.45 bar)

HaemoPharm O4312A); 1T PP Bag + Al Pouch

| Test | | Bulk Solution | Bulk_1M 2-8 | Bulk_1M 40/15 | Bulk_6M 2-8 | Bulk_6M 40/15 | Initial | 1M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.58 | 6.51 | 6.52 | 6.53 | 6.52 | 6.57 | 6.45 | 6.58 | 6.57 | 6.58 |
| Osmolality (mOsm/kg) | | 586 | Not Applicable | | | | 573 | 574 | 569 | 573 | 567 | 571 | 568 | 568 | 568 | 571 |
| LPC | 10μm | Not Applicable | | | | | 1040 | 100 | 73 | 780 | 1167 | 1020 | 113 | 327 | 113 | 107 |
| | 25μm | | | | | | 27 | 7 | 0 | 33 | 53 | 73 | 13 | 20 | 7 | 0 |
| Assay of Anions | % Phosphorus | 97.3 | 101.4 | 103.4 | 101.5 | 115.9 | 98.3 | 101.8 | 100.9 | 101.3 | 101.6 | 101.6 | 101.9 | 102.5 | 102.9 | 102.9 |
| | % Chloride | 96.5 | 99.4 | 101.7 | 100.2 | 115.0 | 96.9 | 99.7 | 98.7 | 102.3 | 101.1 | 102.8 | 102.3 | 100.7 | 101.1 | 101.4 |
| Assay of Cations | % Potassium | 102.1 | 100.9 | 103.5 | 99.1 | 112.0 | 102.3 | 99.5 | 100.3 | 100.6 | 101.3 | 100.9 | 100.6 | 99.6 | 99.9 | 100.0 |
| | % Sodium | 101.1 | 101.2 | 103.9 | 98.8 | 111.8 | 101.2 | 100.1 | 101.1 | 100.0 | 100.6 | 100.5 | 99.5 | 98.3 | 98.5 | 98.5 |

*CCS- A Clear colorless solution, free from visible foreign particles

| Test | | Bulk Solution | Bulk_3M 2-8 | Bulk_3M 40/15 | Bulk_6M 2-8 | Bulk_6M 40/15 | Initial | 3M 25/40 | 1M 40/15 | 3M 2-8 | 3M 25/40 | 3M 40/15 | 6M 2-8 | 6M 25/40 | 6M 30/65 | 6M 40/15 |
|---|---|---|---|---|---|---|---|---|---|---|---|---|---|---|---|---|
| Description* | | CCS | CCS | CCS | CCS | CCS | CCS | CCS | CCS | CCS | CCS | CCS | CCS | CCS | CCS | CCS |
| pH of Solution | | 6.58 | | | | | 6.59 | 6.52 | 6.51 | 6.6 | 6.6 | 6.6 | 6.57 | 6.57 | 6.57 | 6.58 |
| Osmolality (mOsm/kg) | | 580 | Not Applicable | | | | 577 | 568 | 568 | 567 | 568 | 568 | 572 | 576 | 569 | 569 |
| LPC | 10μm | Not Applicable | | | | | 235 | 66 | 47 | 308 | 380 | 127 | 422 | 367 | 613 | 560 |
|  | 25μm | | | | | | 13 | 7 | 0 | 13 | 20 | 13 | 30 | 12 | 27 | 40 |
| Assay of Anions | % Phosphorus | 97.3 | 101.4 | 103.2 | 103.5 | 115.9 | 94.5 | 101.0 | 101.3 | 103.3 | 102.4 | 101.5 | 103.0 | 102.5 | 102.8 | 103.0 |
|  | % Chloride | 96.5 | 99.4 | 103.7 | 100.2 | 103.5 | 97.3 | 99.5 | 99.1 | 104.9 | 102.6 | 102.9 | 101.1 | 100.8 | 101.0 | 101.4 |
| Assay of Cations | % Potassium | 102.3 | 100.9 | 103.5 | 99.1 | 102.0 | 102.9 | 100.2 | 100.0 | 103.2 | 100.2 | 100.3 | 99.9 | 99.6 | 99.7 | 103.1 |
|  | % Sodium | 101.1 | 101.2 | 103.9 | 94.8 | 101.8 | 102.0 | 101.9 | 100.8 | 97.3 | 98.0 | 98.4 | 98.6 | 98.3 | 98.2 | 98.2 |

* CCS - A Clear colorless solution, free from visible foreign particles

Autoclave @ 115°C for 28 Minutes (Autoclave Pressure: Max-2.61 bar, Min-2.45 bar)
TechnoFlex 11 PP Bag - Al Pouch
Condition B. No.#192073_11

Autoclave @ 121°C for 15 Minutes (Autoclave Pressure: Max-3.19 bar, Min-2.99 bar)

Hnoneoflbarm (A1112A), 1T PP Bag + Al Pouch

| Test | | Initial | 1M 2-8 | 1M 25/40 | 1M 40/15 | 3M 2-8 | 3M 25/40 | 3M 30/65 | 3M 40/15 | 6M 2-8 | 6M 25/40 | 6M 30/65 | 6M 40/15 |
|---|---|---|---|---|---|---|---|---|---|---|---|---|---|
| Description* | | CCS | CCS | CCS | CCS | CCS | CCS | CCS | CCS | CCS | CCS | CCS | CCS |
| pH of Solution | | 6.56 | 6.61 | 6.60 | 6.58 | 6.66 | 6.65 | 6.66 | 6.67 | 6.59 | 6.58 | 6.58 | 6.58 |
| Osmolality (mOsm/kg) | | 569 | 579 | 581 | 589 | 576 | 589 | 578 | 577 | 579 | 577 | 573 | 573 |
| LPC | 10μm | 493 | 980 | 553 | 226 | 240 | 187 | 192 | 207 | 337 | 173 | 300 | 80 |
| | 25μm | 13 | 47 | 20 | 7 | 13 | 0 | 13 | 13 | 7 | 20 | 7 | 0 |
| Assay of Anions | % Phosphorus | 100.9 | 98.7 | 98.3 | 99.4 | 102.5 | 104.9 | 104.7 | 103.4 | 98.6 | 100.2 | 99.0 | 99.6 |
| | % Chloride | 100.0 | 97.3 | 97.8 | 98.5 | 101.8 | 104.1 | 104.0 | 102.9 | 99.3 | 100.8 | 99.5 | 100.2 |
| Assay of Cations | % Potassium | 101.8 | 102.7 | 103.4 | 103.0 | 100.0 | 101.8 | 101.7 | 100.7 | 101.8 | 100.0 | 99.2 | 99.8 |
| | % Sodium | 100.7 | 101.9 | 102.5 | 103.0 | 99.0 | 101.0 | 100.8 | 99.9 | 100.3 | 100.8 | 98.0 | 98.6 |

* CCS: A Clear colorless solution, free from visible foreign particles

*FIG.12*

B. No.#VPQ21896

HaemoPharm (M312) 1T PP Bag + Al Pouch
Aseptic Filling

| Test | | Bulk Solution | Initial | 1M 2-8 | 1M 25-40 | 1M 40/15 | 3M 2-8 | 3M 25-40 | 3M 40/65 | 3M 40/15 | 6M 2-8 | 6M 25-40 | 6M 30/65 | 6M 40/15 |
|---|---|---|---|---|---|---|---|---|---|---|---|---|---|---|
| Description* | | CCS | CCS | CCS | CCS | CCS | CCS | CCS | CCS | CCS | CCS | CCS | CCS | CCS |
| pH of Solution | | 6.60 | 6.52 | 6.68 | 6.68 | 6.69 | 6.66 | 6.66 | 6.66 | 6.66 | 6.59 | 6.53 | 6.6 | 6.5 |
| Osmolality (mOsm/kg) | | 561 | 561 | 577 | 575 | 577 | 574 | 577 | 578 | 574 | 572 | 580 | 579 | 580 |
| LPC | 10μm | Not Applicable | 267 | 367 | 347 | 253 | 87 | 127 | 140 | 140 | 260 | 260 | 160 | 260 |
| | 25μm | | 47 | 33 | 13 | 13 | 7 | 13 | 20 | 0 | 7 | 7 | 13 | 27 |
| Assay of Anions | % Phosphorus | 101.2 | 102.0 | 100.6 | 101.6 | 103.3 | 103.0 | 103.0 | 100.5 | 103.1 | 103.2 | 103.7 | 103.8 | 103.0 |
| | % Chloride | 100.0 | 100.1 | 103.2 | 100.9 | 101.0 | 104.1 | 104.2 | 101.3 | 103.1 | 102.8 | 103.5 | 103.7 | 103.3 |
| Assay of Cations | % Potassium | 101.1 | 101.2 | 102.3 | 101.4 | 104.3 | 101.5 | 103.0 | 99.3 | 101.1 | 100.0 | 100.4 | 100.5 | 101.5 |
| | % Sodium | 101.6 | 101.5 | 101.6 | 102.1 | 103.6 | 101.3 | 102.6 | 99.6 | 101.4 | 99.5 | 100.0 | 100.2 | 100.4 |

* CCS- A Clear colorless solution, free from visible foreign particles

Autoclave @ 121°C for 15 Minutes (Autoclave Pressure: Max-3.24 bar, Min-2.89 bar)

HaemoPharm (M312) 1T PP Bag + Al Pouch

| Test | | Bulk Solution | Initial | 1M 2-8 | 1M 25-40 | 1M 40/15 | 3M 2-8 | 3M 25-40 | 3M 40/65 | 3M 40/15 | 6M 2-8 | 6M 25-40 | 6M 30/65 | 6M 40/15 |
|---|---|---|---|---|---|---|---|---|---|---|---|---|---|---|
| Description* | | CCS | CCS | CCS | CCS | CCS | CCS | CCS | CCS | CCS | CCS | CCS | CCS | CCS |
| pH of Solution | | 6.60 | 6.52 | 6.67 | 6.67 | 6.68 | 6.64 | 6.55 | 6.55 | 6.55 | 6.58 | 6.6 | 6.59 | 6.61 |
| Osmolality (mOsm/kg) | | 563 | 569 | 593 | 575 | 578 | 574 | 577 | 573 | 583 | 572 | 580 | 574 | 574 |
| LPC | 10μm | Not Applicable | 507 | 593 | 693 | 447 | 87 | 80 | 153 | 60 | 307 | 1040 | 300 | 127 |
| | 25μm | | 13 | 0 | 20 | 20 | 0 | 0 | 27 | 0 | 13 | 20 | 7 | 13 |
| Assay of Anions | % Phosphorus | 101.2 | 101.7 | 97.0 | 98.7 | 100.8 | 102.1 | 102.6 | 102.5 | 104.2 | 102.4 | 103.9 | 102.5 | 103.7 |
| | % Chloride | 100.0 | 100.6 | 103.1 | 103.3 | 102.7 | 102.5 | 103.4 | 103.2 | 105.0 | 102.2 | 103.8 | 102.3 | 103.5 |
| Assay of Cations | % Potassium | 101.1 | 101.8 | 100.1 | 101.4 | 103.0 | 100.8 | 101.0 | 100.0 | 102.3 | 99.4 | 100.8 | 101.7 | 100.5 |
| | % Sodium | 101.6 | 101.5 | 99.7 | 100.8 | 102.5 | 100.8 | 101.4 | 101.1 | 102.5 | 98.7 | 100.0 | 98.7 | 99.9 |

* CCS- A Clear colorless solution, free from visible foreign particles

*FIG.13*

B. No.8XPQ21887

Aseptic Filling

HaemoPharm (M312) 1L PP Bag + Al Pouch

| Test | | Bulk Solution | Initial | Condition | | | | | | | | | |
|---|---|---|---|---|---|---|---|---|---|---|---|---|---|
| | | | | 1M 2-8 | 1M 25:40 | 1M 40/15 | 3M 2-8 | 3M 25:40 | 3M 30/65 | 3M 40/15 | 6M 2-8 | 6M 25:40 | 6M 30/65 | 6M 40/15 |
| Description* | | CCS | CCS | CCS | CCS | CCS | CCS | CCS | CCS | CCS | CCS | CCS | CCS | CCS |
| pH of Solution | | 6.58 | 6.65 | 6.56 | 6.57 | 6.56 | 6.48 | 6.48 | 6.49 | 6.49 | 6.58 | 6.58 | 6.59 | 6.5 |
| Osmolality (mOsm/kg) | | 575 | 575 | 573 | 574 | 576 | 569 | 575 | 578 | 577 | 565 | 567 | 568 | 569 |
| LPC | 10μm | Not Applicable | 240 | 993.33 | 886.67 | 2166.67 | 473 | 1506 | 578 | 107 | 133 | 567 | 453 | 107 |
| | 25μm | | 7 | 6.67 | 0 | 46.67 | 13 | 13 | 23 | 20 | 13 | 47 | 33 | 7 |
| Assay of Anions | % Phosphorus | 101.9 | 102.2 | 102.9 | 104.9 | 103.1 | 98.0 | 99.2 | 99.7 | 99.0 | 100.5 | 102.0 | 102.4 | 101.9 |
| | % Chloride | 101.5 | 101.8 | 102.8 | 104.6 | 103.2 | 100.0 | 99.2 | 101.7 | 100.2 | 101.1 | 101.0 | 101.6 | 102.1 |
| Assay of Cations | % Potassium | 99.4 | 99.7 | 101.6 | 100.7 | 100.9 | 99.6 | 99.1 | 100.2 | 99.6 | 100.0 | 101.0 | 101.4 | 101.0 |
| | % Sodium | 98.8 | 99.1 | 100.9 | 102.4 | 101.7 | 99.6 | 97.0 | 99.1 | 97.6 | 100.6 | 101.5 | 101.9 | 101.6 |

* CCS- A Clear colorless solution, free from visible foreign particles

Infossed (Polyvin APP11AS) 1L PP Bag + Al Pouch

| Test | | Bulk Solution | Initial | Condition | | | | | | | | | |
|---|---|---|---|---|---|---|---|---|---|---|---|---|---|
| | | | | 1M 2-8 | 1M 25:40 | 1M 40/15 | 3M 2-8 | 3M 25:40 | 3M 30/65 | 3M 40/15 | 6M 2-8 | 6M 25:40 | 6M 30/65 | 6M 40/15 |
| Description* | | CCS | CCS | CCS | CCS | CCS | CCS | CCS | CCS | CCS | CCS | CCS | CCS | CCS |
| pH of Solution | | 6.58 | 6.67 | 6.57 | 6.56 | 6.56 | 6.49 | 6.49 | 6.5 | 6.5 | 6.58 | 6.58 | 6.58 | 6.58 |
| Osmolality (mOsm/kg) | | 573 | 573 | 573 | 571 | 575 | 573 | 580 | 582 | 574 | 580 | 577 | 579 | 578 |
| LPC | 10μm | Not Applicable | 193 | 2893.33 | 3453.33 | 360 | 239 | 313 | 80 | 293 | 73 | 287 | 173 | 1767 |
| | 25μm | | 0 | 360 | 133.33 | 13.33 | 20 | 20 | 7 | 46 | 7 | 7 | 27 | 47 |
| Assay of Anions | % Phosphorus | 101.9 | 102.5 | 103.4 | 100.3 | 102.0 | 99.1 | 97.4 | 98.5 | 98.3 | 103.2 | 103.5 | 103.5 | 103.4 |
| | % Chloride | 101.5 | 102.2 | 100.8 | 100.4 | 102.1 | 100.5 | 100.7 | 99.6 | 99.7 | 103.5 | 103.7 | 103.8 | 103.8 |
| Assay of Cations | % Potassium | 99.4 | 100.1 | 102.5 | 99.7 | 100.9 | 100.4 | 99.1 | 100.7 | 99.7 | 101.9 | 101.8 | 101.5 | 101.6 |
| | % Sodium | 98.8 | 99.4 | 102.5 | 98.3 | 100.8 | 97.2 | 95.9 | 97.7 | 96.1 | 102.5 | 102.3 | 102.3 | 102.1 |

* CCS- A Clear colorless solution, free from visible foreign particles

FIG.14

| | | | | | | Autoclave @ 121°C for 15 Minutes (Autoclave Pressure: Max-3.16 bar, Min-2.97 bar) | | | | | | |
| | | | | | | HaemoPharm (A012) IT PP Bag + Al Pouch | | | | | | |
| Test | | Bulk Solution | Initial | 3M 2-8 | 3M 25-40 | 3M 40/15 | 3M 30/65 | 3M 40/15 | 6M 2-8 | 6M 25-40 | 6M 30/65 | 6M 40/15 |
| Description* | | CCS | CCS | CCS | CCS | CCS | CCS | CCS | CCS | CCS | CCS | CCS |
| pH of Solution | | 6.58 | 6.63 | 6.57 | 6.56 | 6.57 | 6.49 | 6.49 | 6.59 | 6.59 | 6.59 | 6.59 |
| Osmolality (mOsm/kg) | | 577 | 581 | 572 | 574 | 589 | 578 | 569 | 568 | 570 | 586 | |
| LPC | 10μm | Not Applicable | 473 | 313.33 | 2093.33 | 646.67 | 233 | 100 | 21 | 266 | 413 | |
| | 25μm | | 26 | 46 | 26 | 46.67 | 27 | 7 | 27 | 20 | 46 | 60 |
| Assay of Anions | % Phosphorus | 101.9 | 102.1 | 103.9 | 103.7 | 104.0 | 98.7 | 100.9 | 102.3 | 103.0 | 103.2 | 102.1 |
| | % Chloride | 101.5 | 102.0 | 106.4 | 105.9 | 104.9 | 99.7 | 103.6 | 102.5 | 103.4 | 103.4 | 103.2 |
| Assay of Cations | % Potassium | 99.4 | 99.9 | 103.1 | 102.1 | 103.9 | 99.9 | 101.3 | 106.8 | 103.0 | 101.2 | 100.9 |
| | % Sodium | 98.8 | 99.5 | 101.1 | 102.2 | 102.6 | 97.3 | 98.5 | 101.1 | 101.5 | 101.7 | 101.5 |

* CCS - A Clear colorless solution, free from visible foreign particles

| | | | | | | Autoclave @ 121°C for 15 Minutes (Autoclave Pressure: Max-3.29 bar, Min-2.97 bar) | | | | | | |
| | | | | | | Infomed (Polvin APP114S) IT PP Bag + Al Pouch | | | | | | |
| Test | | Bulk Solution | Initial | 3M 2-8 | 3M 25-40 | 3M 40/15 | 3M 30/65 | 3M 40/15 | 6M 2-8 | 6M 25-40 | 6M 30/65 | 6M 40/15 |
| Description* | | CCS | CCS | CCS | CCS | CCS | CCS | CCS | CCS | CCS | CCS | CCS |
| pH of Solution | | 6.58 | 6.65 | 6.57 | 6.57 | 6.57 | 6.5 | 6.49 | 6.58 | 6.58 | 6.58 | 6.58 |
| Osmolality (mOsm/kg) | | 573 | 573 | 589 | 589 | 569 | 572 | 576 | 570 | 579 | 573 | 571 |
| LPC | 10μm | Not Applicable | 120 | 393.33 | 853.33 | 3166.67 | 127 | 53.3 | 107 | 120 | 147 | 367 |
| | 25μm | | 7 | 20 | 13.33 | 91.33 | 7 | 27 | 7 | 13 | 0 | 13 | 20 |
| Assay of Anions | % Phosphorus | 101.9 | 101.6 | 105.1 | 104.4 | 104.3 | 98.4 | 98.5 | 103.8 | 102.8 | 103.1 | 102.8 |
| | % Chloride | 101.5 | 101.6 | 106.3 | 106.7 | 105.2 | 99.5 | 99.8 | 104.0 | 103.6 | 103.3 | 103.9 |
| Assay of Cations | % Potassium | 99.4 | 99.6 | 101.4 | 104.1 | 103.2 | 99.2 | 99.7 | 102.1 | 101.3 | 101.4 | 101.1 |
| | % Sodium | 98.8 | 99.6 | 100.1 | 103.1 | 102.6 | 98.2 | 98.1 | 102.3 | 101.6 | 101.8 | 101.4 |

* CCS - A Clear colorless solution, free from visible foreign particles

B. No.#NPO21012

Autoclave @ 121°C for 15 Minutes (Autoclave Pressure: Max-3.24 bar, Min-2.99 bar)

Infomed (Nexcel M312) 1T PP Bag + Al Pouch

| Test | | Bulk Solution | Initial | Condition | | | | | | |
|---|---|---|---|---|---|---|---|---|---|---|
| | | | | 1M 2-8 | 1M 25/40 | 1M 40/15 | 3M 2-8 | 3M 25/40 | 3M 30/65 | 3M 40/15 |
| Description* | | CCS | CCS | CCS | CCS | CCS | CCS | CCS | CCS | CCS |
| pH of Solution | | 6.53 | 6.54 | 6.56 | 6.62 | 6.61 | 6.59 | 6.56 | 6.55 | 6.57 |
| Osmolality (mOsm/kg) | | 573 | 574 | 570 | 565 | 569 | 569 | 572 | 572 | 568 |
| LPC | 10μm | 67 | 320 | 720 | 380 | 520 | 227 | 227 | 1125 | 187 |
| | 25μm | 0 | 20 | 100.67 | 53.33 | 33.33 | 0 | 7 | 33 | 7 |
| Assay of Anions | % Phosphorus | 101.7 | 101.6 | 98.5 | 98.1 | 98.9 | 101.1 | 100.9 | 100.9 | 100.6 |
| | % Chloride | 99.7 | 99.4 | 99.2 | 99.7 | 99.5 | 98.9 | 99.2 | 98.8 | 98.5 |
| Assay of Cations | % Potassium | 101.7 | 101.5 | 99.2 | 98.9 | 99.8 | 100.1 | 100.3 | 99.9 | 99.6 |
| | % Sodium | 99.3 | 99.2 | 98.3 | 97.3 | 98.2 | 98.8 | 99.1 | 98.9 | 98.4 |

* CCS- A Clear colorless solution, free from visible foreign particles

Autoclave @ 121°C for 15 Minutes (Autoclave Pressure: Max-3.24 bar, Min-2.99 bar)

Infomed (Polycine APP11.A5) 1T PP Bag + Al Pouch

| Test | | Bulk Solution | Initial | Condition | | | | | | |
|---|---|---|---|---|---|---|---|---|---|---|
| | | | | 1M 2-8 | 1M 25/40 | 1M 40/15 | 3M 2-8 | 3M 25/40 | 3M 30/65 | 3M 40/15 |
| Description* | | CCS | CCS | CCS | CCS | CCS | CCS | CCS | CCS | CCS |
| pH of Solution | | 6.53 | 6.54 | 6.55 | 6.54 | 6.54 | 6.57 | 6.56 | 6.56 | 6.58 |
| Osmolality (mOsm/kg) | | 573 | 573 | 570 | 570 | 570 | 568 | 570 | 566 | 570 |
| LPC | 10μm | 67 | 153 | 1526.67 | 2053.33 | 1193.33 | 893 | 287 | 647 | 193 |
| | 25μm | 0 | 0 | 6.67 | 13.33 | 20 | 13 | 27 | 13 | 0 |
| Assay of Anions | % Phosphorus | 101.7 | 101.2 | 98.8 | 98.0 | 97.8 | 100.6 | 99.8 | 100.7 | 100.5 |
| | % Chloride | 99.7 | 99.2 | 99.9 | 98.4 | 98.4 | 99.8 | 98.6 | 98.6 | 98.4 |
| Assay of Cations | % Potassium | 101.7 | 101.2 | 99.9 | 98.6 | 98.5 | 100.9 | 99.6 | 99.9 | 99.6 |
| | % Sodium | 99.3 | 98.9 | 98.3 | 97.1 | 96.9 | 99.9 | 98.4 | 98.6 | 98.4 |

* CCS- A Clear colorless solution, free from visible foreign particles

*FIG. 16*

| Engineering Batch_Lot#21070832 (Finished Product) | | | | |
|---|---|---|---|---|
| Autoclave @ 121°C for 15 Minutes | | | | |
| Infomed (Nexcel M312) 1T PP Bag + Al Pouch | | | | |
| Test | Condition | | | |
| | Bulk Solution | | | Initial |
| | Sampling Time: 5 Minutes | Sampling Time: 10 Minutes | Sampling Time: 15 Minutes | |
| Description* | CCS | CCS | CCS | CCS |
| pH of Solution | 6.64 | 6.63 | 6.64 | 6.61 |
| Osmolality (mOsm/kg) | 559 | 556 | 555 | 566 |
| LPC 10µm | 1006.67 | 466.67 | 300 | 60 |
| LPC 25µm | 66.67 | 40 | 13.33 | 0 |
| Assay of Anions % Phosphorus | 98.7 | 98.2 | 97.8 | 98.6 |
| Assay of Anions % Chloride | 98.9 | 98.7 | 98.0 | 98.9 |
| Assay of Cations % Potassium | 99 | 98.7 | 97.8 | 99.0 |
| Assay of Cations % Sodium | 97.3 | 96.7 | 95.9 | 97.3 |

* CCS- A Clear colorless solution, free from visible foreign particles

| Autoclave @ 121°C for 15 Minutes | | | | |
|---|---|---|---|---|
| Infomed (Polycine APP114S) 1T PP Bag + Al Pouch | | | | |
| Test | Condition | | | |
| | Bulk Solution | | | Initial |
| | Sampling Time: 5 Minutes | Sampling Time: 10 Minutes | Sampling Time: 15 Minutes | |
| Description* | CCS | CCS | CCS | CCS |
| pH of Solution | 6.64 | 6.63 | 6.64 | 6.61 |
| Osmolality (mOsm/kg) | 559 | 556 | 555 | 564 |
| LPC 10µm | 1006.67 | 466.67 | 300 | 260 |
| LPC 25µm | 66.67 | 40 | 13.33 | 46.67 |
| Assay of Anions % Phosphorus | 98.7 | 98.2 | 97.8 | 98.8 |
| Assay of Anions % Chloride | 98.9 | 98.7 | 98.0 | 98.9 |
| Assay of Cations % Potassium | 99 | 98.7 | 97.8 | 99.5 |
| Assay of Cations % Sodium | 97.3 | 96.7 | 95.9 | 97.5 |

* CCS- A Clear colorless solution, free from visible foreign particles

*FIG.17*

| Aseptic Filling ||||||
|---|---|---|---|---|---|
| Infomed (Nexcel M312) 1T PP Bag + Al Pouch ||||||
| Test || Condition ||||
| || Bulk Solution ||| Sampling: Beginning |
| || Sampling Time: 5 Minutes | Sampling Time: 10 Minutes | Sampling Time: 15 Minutes | |
| Description* || CCS | CCS | CCS | CCS |
| pH of Solution || 6.64 | 6.63 | 6.64 | 6.61 |
| Osmolality (mOsm/kg) || 559 | 556 | 555 | 562 |
| LPC | 10μm | 1006.67 | 466.67 | 300 | 66.67 |
| | 25μm | 66.67 | 40 | 13.33 | 0 |
| Assay of Anions | % Phosphorus | 98.7 | 98.2 | 97.8 | 99.7 |
| | % Chloride | 98.9 | 98.7 | 98.0 | 99.9 |
| Assay of Cations | % Potassium | 99 | 98.7 | 97.8 | 99.5 |
| | % Sodium | 97.3 | 96.7 | 95.9 | 97.8 |
| * CCS- A Clear colorless solution, free from visible foreign particles ||||||

| Aseptic Filling ||||||
|---|---|---|---|---|---|
| Infomed (Polycine APP114S) 1T PP Bag + Al Pouch ||||||
| Test || Condition ||||
| || Bulk Solution ||| Sampling: Beginning |
| || Sampling Time: 5 Minutes | Sampling Time: 10 Minutes | Sampling Time: 15 Minutes | |
| Description* || CCS | CCS | CCS | CCS |
| pH of Solution || 6.64 | 6.63 | 6.64 | 6.61 |
| Osmolality (mOsm/kg) || 559 | 556 | 555 | 560 |
| LPC | 10μm | 1006.67 | 466.67 | 300 | 453.33 |
| | 25μm | 66.67 | 40 | 13.33 | 33.33 |
| Assay of Anions | % Phosphorus | 98.7 | 98.2 | 97.8 | 98.3 |
| | % Chloride | 98.9 | 98.7 | 98.0 | 98.4 |
| Assay of Cations | % Potassium | 99 | 98.7 | 97.8 | 98.3 |
| | % Sodium | 97.3 | 96.7 | 95.9 | 96.3 |
| * CCS- A Clear colorless solution, free from visible foreign particles ||||||

*FIG.17 cont'd*

| Engineering Batch_Lot#21070832 (Placebo) |||||
|---|---|---|---|---|
| Autoclave @ 121°C for 15 Minutes |||||
| Infomed (Nexcel M312) 1T PP Bag + Al Pouch |||||
| Test || Condition ||  Initial |
| || Bulk Solution |||
| || Sampling Time: 5 Minutes | Sampling Time: 10 Minutes | Sampling Time: 15 Minutes | |
| Description* ||||CCS |
| pH of Solution |||| 6.28 |
| Osmolality (mOsm/kg) |||| 289 |
| LPC | 10µm | NA || 813.33 |
| | 25µm | || 13.33 |
| Assay of Anions | % Phosphorus | || NA |
| | % Chloride | || 100.0 |
| Assay of Cations | % Potassium | || NA |
| | % Sodium | || 99.1 |
| * CCS- A Clear colorless solution, free from visible foreign particles |||||

| Autoclave @ 121°C for 15 Minutes |||||
|---|---|---|---|---|
| Infomed (Polycine APP114S) 1T PP Bag + Al Pouch |||||
| Test || Condition || Initial |
| || Bulk Solution |||
| || Sampling Time: 5 Minutes | Sampling Time: 10 Minutes | Sampling Time: 15 Minutes | |
| Description* ||||CCS |
| pH of Solution |||| 6.3 |
| Osmolality (mOsm/kg) |||| 287 |
| LPC | 10µm | NA || 806.67 |
| | 25µm | || 6.67 |
| Assay of Anions | % Phosphorus | || NA |
| | % Chloride | || 100.9 |
| Assay of Cations | % Potassium | || NA |
| | % Sodium | || 99.4 |
| * CCS- A Clear colorless solution, free from visible foreign particles |||||

*FIG.17 cont'd*

| | | | | B. No.:#NPO2054 | | | | | | |
|---|---|---|---|---|---|---|---|---|---|---|
| Test | | AsepticFilling | TS @ 121°C for 15 Minutes | | | | TS @ 115°C for 20 Minutes | | | |
| | | Bulk Solution | TechnoFlex_1T Bag | Grifols_1T Bag | TechnoFlex_2T Bag | Bausch_2T Bag | TechnoFlex PVC_2T Bag | TechnoFlex_1T Bag | Grifols_1T Bag | TechnoFlex_2T Bag | Bausch_2T Bag | TechnoFlex PVC_2T Bag |
| Description* | | CCS | CCS | CCS | CCS | CCS | CCS | CCS | CCS | CCS | CCS | CCS |
| pH of Solution | | 6.628 | 6.627 | 6.634 | 6.629 | 6.626 | 6.623 | 6.621 | 6.623 | 6.628 | 6.61 | 6.605 |
| Osmolality (mOsm/kg) | | 318 | 318 | 319 | 318 | 319 | 323 | 322 | 321 | 320 | 320 | 321 |
| LPC | 10μm | 587 | 133 | 80 | 67 | 80 | 193 | 313 | 133 | 100 | 87 | 140 |
| | 25μm | 0 | 7 | 7 | 0 | 20 | 20 | 0 | 13 | 0 | 13 | 7 |
| Assay of Anions | % Phosphorus | 102.3 | 102.1 | 101.9 | 101.7 | 101.6 | 102.3 | 102.1 | 103.0 | 102.3 | 101.7 | 103.9 |
| | % Chloride | 101.8 | 102.3 | 102.6 | 102.4 | 102.1 | 103.0 | 102.8 | 103.3 | 102.6 | 102.4 | 104.6 |
| Assay of Cations | % Potassium | 100.5 | 100.6 | 100.8 | 101.3 | 101.0 | 100.7 | 101.1 | 101.5 | 100.8 | 100.7 | 103.1 |
| | % Sodium | 99.0 | 99.6 | 100.0 | 99.7 | 99.5 | 99.9 | 99.8 | 100.3 | 99.5 | 99.4 | 101.7 |

READY-TO-USE POTASSIUM PHOSPHATES IN SODIUM CHLORIDE SOLUTIONS

This application is a continuation-in-part application of our copending US non-provisional application with the Ser. No. 17/499,001, which was filed Oct. 12, 2021, and which claims priority to our provisional application with the Ser. No. 63/090,518, which was filed Oct. 12, 2020, all of which are incorporated by reference herein.

FIELD OF THE INVENTION

The field of the invention is compositions and methods for potassium phosphates solutions for injection, especially as it relates to such solutions with ultra-low concentrations of aluminum where the solutions are packaged in a ready-to-use container at volumes and concentrations suitable for direct administration to a patient.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Hypophosphatemia is a clinical condition in which serum phosphate concentrations are less than 2.5 mg/dL (0.81 mmol/L). Causes for such condition can include alcohol use disorder, burns, starvation, and diuretic use, and symptoms include muscle weakness, respiratory failure, heart failure, and seizures and coma can occur. In most cases, the treatment for hypophosphatemia is phosphorus replacement therapy with an intravenous (TV) infusion rate of phosphates that must be adjusted to the patient's age and particular need. Phosphorus replacement therapy is generally administered via peripheral venous catheter or central venous catheter and at a rate according to the maximum recommended concentration and infusion rates of a known commercially available product (Potassium Phosphates injection, USP, Fresenius Kabi) are shown in Table 1 (Maximum Recommended Daily Concentration of Potassium Phosphates Injection By Age and Route of Administration (Peripheral vs. Central)) and Table 2 (Maximum Recommended Infusion Rate of Potassium Phosphates Injection For Adults and Pediatric Patients 12 Years of Age and Older), where the term 'Phosphorus' is equivalent with 'Phosphate' ($PO_4^{3-}$ anion).

TABLE 1

| Patient Population | Peripheral Venous Catheter | Central Venous Catheter |
| --- | --- | --- |
| Adults and Pediatric Patients (12 Years of Age and Older) | Phosphorus 6.8 mmol/100 mL (Potassium 10 mEq/100 mL) | Phosphorus 18 mmol/100 mL (Potassium 26.4 mEq/100 mL) |
| Pediatric Patients (Less than 12 Years of Age) | Phosphorus 0.27 mmol/10 mL (Potassium 0.4 mEq/10 mL) | Phosphorus 0.55 mmol/10 mL (Potassium 0.8 mEq/10 mL) |

TABLE 2

| Route of Administration | Maximum Infusion Rate |
| --- | --- |
| Peripheral Venous Catheter | Phosphorus 6.8 mmol/hour (Potassium 10 mEq/hour) |
| Central Venous Catheter | Phosphorus 15 mmol/hour (Potassium 22 mEq/hour) |

Currently approved phosphorus replacement products of potassium phosphorus for IV administration may require continuous electrocardiographic (ECG) monitoring as serious cardiac reactions may occur as well as pulmonary embolisms due to pulmonary vascular precipitates. These serious cardiac and pulmonary risk factors render the accuracy of the concentration and infusion rate of the potassium phosphate critical for patient safety. Furthering these risks, the currently approved potassium phosphorus products are supplied and stored as concentrates and will therefore require aseptic compounding for the needed infusion rate, thereby increasing the risk of error and contamination. While care and monitoring may be implemented to avoid miscalculations, contamination, and serious adverse effects, preparing the IV solution by dilution and programming the correct infusion rate for administration often takes time and additional oversight. Furthermore, in most cases separate preparations are required for each of the central venous and peripheral venous administrations.

In addition, there are also potential risks with respect to chemical stability and aluminum toxicity, especially in patients with renal impairment. As is well known, phosphate solutions may be subject to crystallization and precipitation, which is exacerbated in the presence of oxygen. For that reason, concentrated solutions must be used within several hours as any remaining volume of such solutions after even limited exposure to oxygen is prone to crystallization and precipitation. To reduce the risk of crystallization during storage, deoxygenated preparations can be prepared as is described in CN106265499. However, such formulations were nevertheless concentrates and as such failed to avoid many of the difficulties associated with concentrates. With respect to levels of aluminum it should be recognized that while most currently used products are below the maximum allowed aluminum level as determined by the Federal Drug Administration (FDA), some of these aluminum concentrations may nevertheless be toxic in impaired patients. Attempts have been made to produce potassium phosphate compositions with decreased concentrations of aluminum as is disclosed, for example, in U.S. Ser. No. 10/632,150. However, the products described in the '150 patent are still concentrates, and problems associated with such forms remain. Moreover, many of the known concentrated compositions include varying amounts of potassium in the form of potassium dihydrogen phosphate and potassium hydrogen phosphate and may not provide a proper ratio of these critical components, nor do these compositions provide a tonicity agent.

Therefore, there is still a need for potassium phosphates solutions with reduced aluminum content where such solutions are in a ready-to-administer formulation suitable for phosphorus replacement therapy, and where such solutions have sufficient storage stability.

SUMMARY OF THE INVENTION

The inventive subject matter is directed to various compositions and methods of ready-to-use (RTU) potassium phosphates solutions for intravenous administration to patients in need thereof. Advantageously, the solutions presented herein exhibit excellent storage stability over extended periods of time, include a suitable tonicity agent, have a desirable phosphate to potassium ratio, and have an aluminum content that is equal or less than 50 mcg/L. Such solutions will not require any dilution or other manipulation to adjust the solution to a required phosphate and/or potassium concentration and can be administered as a single unit at a rate of administration that will not require specific calculations.

In one aspect of the inventive subject matter, the inventors contemplate an isotonic or hyper-isotonic sterile ready-to-use (RTU) aqueous potassium phosphates solution that comprises potassium phosphates and sodium chloride, wherein the solution includes 15 mmol/100 ml phosphorus (0.15 mmol/mL) and equal or less than 50 mcg/L aluminum.

In some embodiments, the potassium phosphates comprise potassium dihydrogen phosphate ($KH_2PO_4$) and potassium hydrogen phosphate ($K_2HPO_4$), wherein the potassium dihydrogen phosphate is present in the solution an amount of about 1,120 mg/100 ml (8.2 mmol/100 ml) phosphorus wherein the potassium hydrogen phosphate is present in the solution in an amount of about 1,180 mg/100 ml (6.8 mmol/100 ml) phosphorus, and/or wherein potassium is present in the solution in an amount of about 22 mEq/100 mL. Preferably, but not necessarily, sodium chloride is present in the solution in an amount of about 900 mg/100 ml, and/or the solution has a pH of between 6.2 and 6.8.

In further embodiments, the solution may have, after autoclaving and storage of at least 3 months at 25° C. and 40% relative humidity, a liquid particle count of no more than 360 and 30 for particles having a particle size of equal to or greater than 15 and equal to or greater than 25 micrometer size, respectively. Moreover, the solution may have, after autoclaving and storage of at least 3 months at 25° C. and 40% relative humidity, a change in phosphorus of no more than 1% absolute, and/or the solution may have, after autoclaving and storage of at least 3 months at 25° C. and 40% relative humidity, a change in potassium of no more than 2% absolute. It is further generally preferred that the solution is packaged in a flexible (e.g., polyolefin) container, typically at a volume of 100 mL, and the flexible polyolefin container may further be contained in a secondary metallized overwrap.

Therefore, in still further contemplated aspects, the inventors contemplate a sterile ready-to-use (RTU) premixed pharmaceutical product stored in a flexible polymeric container. While not limiting to the inventive subject matter, the pharmaceutical product may include potassium phosphates in an aqueous sodium chloride solution, containing (a) less than 50 mcg/L aluminum, (b) about 15 mmol/100 ml phosphorus, and (c) about 22 mEq/100 mL potassium.

Most typically, the potassium phosphates comprise potassium dihydrogen phosphate ($KH_2PO_4$) and potassium hydrogen phosphate ($K_2HPO_4$), wherein the potassium dihydrogen phosphate is present in the solution an amount of about 1,120 mg/100 ml (8.2 mmol/100 ml) phosphorus, and wherein the potassium hydrogen phosphate is present in the solution in an amount of about 1,180 mg/100 ml (6.8 mmol/100 ml) phosphorus. It is further preferred that sodium chloride is present in the aqueous sodium chloride solution in an amount of about 900 mg/100 ml.

The premixed pharmaceutical product in the flexible polymeric container preferably has a volume of 100 mL, and it is further preferred that the flexible polymeric container is enclosed in a secondary metallized overwrap. Therefore, in some embodiments, the premixed pharmaceutical product will comprise about 4.65 mg/mL of phosphorus (0.15 mmol/mL), about 8.50 mg/mL of potassium (0.22 mEq/mL), about 3.57 mg/mL of sodium, and about 5.43 mg/mL of chloride.

In a still further aspect of the inventive subject matter, the inventors also contemplate a method of administering phosphates to a patient in need of phosphorus replacement therapy, and contemplated methods include a step of administering, without prior dilution, an isotonic or hyper-isotonic, sterile, and ready-to-use (RTU) solution comprising potassium phosphates and sodium chloride solution from a flexible container to the patient at a rate of infusion and by a route of administration corresponding to the patient's age and degree of need of phosphorus replacement. Most typically, the solution comprises about 15 mmol/100 ml phosphorus, about 22 mEq/100 mL potassium, and less than 50 mcg/L aluminum. In further contemplated embodiments, the rate of infusion is 6.8 mmol phosphates per hour or 15 mmol phosphates per hour, and/or the route of administration is a central venous catheter. Furthermore, it is contemplated that the solution can be administered after extended storage (e.g., storage for at least 3 months at 25° C. and 40% relative humidity).

Various objects, features, aspects and advantages of the inventive subject matter will become more apparent from the following detailed description of preferred embodiments, along with the accompanying drawing figures.

BRIEF DESCRIPTION OF THE DRAWINGS

FIG. 3 is an exemplary flow chart for producing an exemplary solution presented herein.

FIGS. 9-19 are tables providing results for stability conditions for exemplary phosphorus solution as presented herein in various container materials.

DETAILED DESCRIPTION

Figure 1:
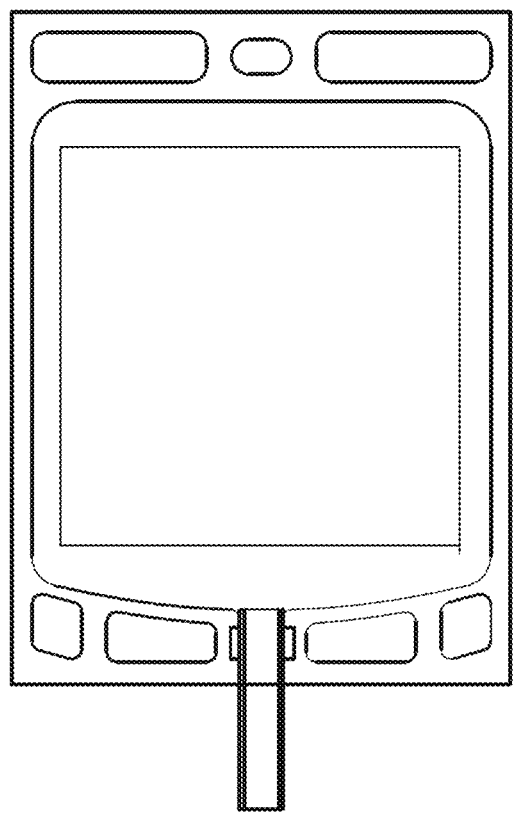
FIG. 1 is an exemplary schematic showing a flexible pouch configuration for storage of the solutions presented herein.

The inventors have now discovered that potassium phosphates solutions can be prepared that are storage stable, sterile, and ready-to-use (RTU), and as such avoid all of the drawbacks of heretofore known concentrated potassium phosphates solutions that required prior manipulation and had no significant shelf life. Moreover, the potassium phosphates solutions presented herein also exhibit a desirably low aluminum concentration and provide phosphates and potassium at ratios that are suitable for facile administration. Still further, the solutions according to the inventive subject matter are preservative free and have osmolality and pH suitable for direct administration.

For example, 100 mL of the RTU solution may be packaged into a flexible polymeric container to thereby provide in a sodium chloride solution about 15 mmol total phosphates and about 22 mEq potassium for injection, wherein the RTU solution has equal or less than 50 micrograms/liter (mcg/L or µg/L) aluminum. It should be appreciated that such RTU solution allows for simple and direct administration to a patient without the need for further dilution or other manipulation, and that such solution can be infused via a pump at a single infusion rate to thereby deliver appropriate quantities of phosphates and potassium. Moreover, and as described in more detail below, the solutions as presented herein also exhibit excellent storage stability (i.e., will not be subject to crystallization and precipitation and remain free of microbial growth). Having the specified quantities of phosphates and potassium will advantageously enable administration to an adult or pediatric patient via peripheral venous administration or central venous administration.

Therefore, especially preferred premixed pharmaceutical products that provide a desirable phosphates to potassium ratio will be prepared such that the solution will contain in water 11.2 mg/mL $KH_2PO_4$ and 11.8 mg/mL $K_2HPO_4$ for a total 0.15 mmol/mL of phosphates, and 9 mg/mL sodium chloride. Notably, such solutions will not only result in a pH suitable for injection (i.e., pH between 6.0 and 7.0), but also result in a ratio of potassium to phosphorus and overall quantities of potassium and phosphorus desirable or necessary for direct injection. Most typically, the potassium phosphates comprise potassium dihydrogen phosphate ($KH_2PO_4$) and potassium hydrogen phosphate ($K_2HPO_4$) at a molar ratio of about 0.7 to 1.3, or about 0.8 to 1.2, or about 1.2 to 1.0.

In this context it is noted that the term "ready-to-use" or "RTU" when used in conjunction with the solutions presented herein refers to a solution that can be directly administered to a patient without prior need for dilution or other adjustment such as addition of saline or other tonicity agent). Viewed from a different perspective, a "ready-to-use" or "RTU" solution can be delivered from a storage container via peripheral or central catheter to a patient without additional manipulation of the solution in the storage container. Therefore, the terms "ready-to-use" and "RTU" are interchangeably used with the term "ready-to-administer". Moreover, the term "phosphorus" is used interchangeably with the term "phosphate" or "phosphates" and refers to the $PO_4^{3-}$ anion, regardless of its protonation state and/or presence of counterion(s). Thus, the term phosphorus can refer to $K_2HPO_4$, $KH_2PO_4$, $HPO_4^{2-}$, $H_2PO_4^-$, and/or $PO_4^{3-}$. Still further, the term "aluminum" as used herein refers to both aluminum ions (e.g., $Al^{3+}$) as well as metallic aluminum. Likewise, the terms "sodium" and "potassium" as used herein refer to the cationic forms of sodium ($Na^+$) and potassium ($K^+$).

In addition to the contemplated RTU potassium phosphates in sodium chloride solution being more efficient, effective, and safe (e.g., less risk of contamination) to prepare and administer, the potassium phosphates in sodium chloride solution also has preferably less than 50 mcg/L aluminum. However, contemplated solutions are also suitable that have less than 100 mcg/L, less than 90 mcg/L, less than 80 mcg/L, less than 70 mcg/L, less than 60 mcg/L, or less than 55 mcg/L aluminum. More preferably, the potassium phosphates in sodium chloride solution has an aluminum content of no more than 50 mcg/L, not more than 49 mcg/L, not more than 48 mcg/L, not more than 47 mcg/L, not more than 46 mcg/L, 45 mcg/L, 44 mcg/L, 43 mcg/L, 42 mcg/L, 41 mcg/L, 40 mcg/L, 39 mcg/L, 38 mcg/L, 37 mcg/L, 36 mcg/L, 35 mcg/L, 34 mcg/L, 33 mcg/L, 32 mcg/L, 31 mcg/L, 30 mcg/L, 29 mcg/L, 28 mcg/L, 27 mcg/L, 26 mcg/L, 25 mcg/L, 24 mcg/L, 23 mcg/L, 22 mcg/L, 21 mcg/L, or 20 mcg/L, and even less (8 mcg/L). Therefore, and most typically, the contemplated potassium phosphates in sodium chloride solution has equal or less than 50 mcg/L, or equal or less than 40 mcg/L, or equal or less than 50 mcg/L aluminum.

Therefore, in exemplary embodiments, the RTU potassium phosphates in sodium chloride solution includes potassium dihydrogen phosphate ($KH_2PO_4$) and potassium hydrogen phosphate ($K_2HPO_4$). Typically, the potassium dihydrogen phosphate is at an amount of about 1120 mg/100 ml (8.2 mmol/100 ml of phosphorus) and the potassium hydrogen phosphate is at an amount of about 1180 mg/100 ml (6.8 mmol/100 ml of phosphorus). Additionally, the sterile RTU aqueous potassium phosphates in sodium chloride solution includes the sodium chloride at an amount of about 900 mg/100 ml.

Moreover, it is pointed out that contemplated methods of making aqueous potassium phosphates in sodium chloride solutions for phosphorus replacement therapy include adding potassium hydrogen phosphate, potassium dihydrogen phosphate, and sodium chloride to water, wherein each of these components does not contain more than 5 part per million (ppm) or more than 4 ppm, or more than 3 ppm, or more than 2 part per million (ppm, approximately 0.7 mmol/100 ml), or more than 1 ppm aluminum. Accordingly, and in contrast to the currently available products, aluminum content is reduced from the starting materials, thereby avoiding any further compounding of aluminum levels and decreasing the levels of total aluminum in the solutions presented herein.

In still further contemplated aspects, it is preferred that the solutions presented herein are stored in an autoclavable flexible container that is most typically fabricated from a polymeric material. Notably, and as shown in more detail below, the inventors also discovered that type of polymeric material may have an impact on chemical and storage stability. For example, some polymeric materials were prone to produce higher quantities of crystallized material and/or precipitates (e.g., at an average particle size of about 10 micron or 25 micron), whereas certain other materials were unexpectedly prone to water loss due to water vapor permeability, particularly at extended periods of storage (e.g., one to several months). Therefore, the inventors also used secondary overwraps that contained the primary packaging materials to help maintain predetermined concentration of all solutes. Among other materials, particularly preferred overwrap materials comprised polymeric composite films with at least one metal (e.g., aluminum) layer.

Figure 2:
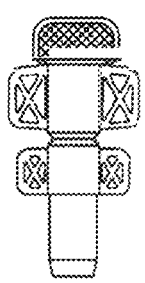
FIG. 2 is an exemplary schematic of a double winged stopper for use with a container of FIG. 1.

With respect to suitable polymeric autoclavable containers, various materials are deemed suitable for use herein, and especially preferred polymeric materials include polysulfone, polycarbonate, polypropylene, polyethylene (LDPE or HDPE), ethylene/propylene copolymers, polyolefins, acrylic-imide copolymers, polyester (e.g., PET, PEN and the like), Teflon, Nylon, acetal (Delrin), polymethylpentene, PVDC, ethylvinylacetate, polyvinyl chloride, and polyolefins. Notably, polyolefin containers remained transparent and dimensionally stable, even after autoclaving and were as such preferred. As will be readily appreciated, the polymeric containers can be prepared in numerous form factors, however, flexible bags are especially preferred. Likewise, the volume of the polymeric container may change considerably. However, it is typically preferred that the container has a volume that accommodates the volume of solution required for a single and complete administration of the solutions presented herein. Therefore, a particularly preferred internal volume of the container is 100 mL. Moreover, it should be appreciated that the polymeric container will have a single or a double port that is typically sealed with a stopper as is well known in the art. FIG. 1 depicts an exemplary flexible container with 100 mL internal volume, and FIG. 2 depicts an exemplary double winged stopper that can be used with the container of FIG. 1.

Most typically, the potassium phosphates in sodium chloride solution in the flexible container will be sterilized in the container by steam sterilization (e.g., autoclaving, 121° C. for about 15 minutes), preferably without altering the thermal properties of the film layers, ports, and closure system as well as maintaining the integrity of the flexible container. In more typical embodiments, the premixed or ready-to-use stable pharmaceutical, formulation of potassium phosphates in sodium chloride at 15 mmol/100 ml of Phosphorus is packaged in a non-PVC plastic container with ports and container closure systems, which is terminally sterilized at a temperature of at least about 110° C. to 130° C. via autoclaving with a dwelling time ranging from 7 to 30 minutes.

Within these embodiments, it is preferred that the autoclaving temperature ranges from 110 to 130° C. The autoclaving temperature can be at a minimum temperature of 111° C., 112° C., 113° C., 114° C., 115° C., 116° C., 117° C., 118° C., 119° C., 120° C., or 121° C., and the maximum temperature can be 130° C., 129° C., 128° C., 127° C., 126° C., 125° C., 124° C., 123° C., 122° C., 121° C., or 120° C., inclusive of all ranges and sub-ranges embraced therein. Therefore, typical ranges for the autoclaving temperature may be include from 111 to 131° C., or from 117 to 125° C. Within these embodiments, it is preferred that the autoclaving time range from 7 to 60 minutes. The autoclaving time can be at a minimum of 7 minutes, 9 minutes, 11 minutes, 13 minutes or 15 minutes and the maximum autoclaving time can be 60 minutes, 45 minutes 30 minutes, 28 minutes, 26 minutes, 25 minutes, 24 minutes, 22 minutes, or 20 minutes, inclusive of all ranges and sub-ranges embraced therein. Exemplary ranges for the autoclaving time include from 7 to 60 minutes, or from 8 to 45 minutes, or from 9 to 30 minutes, or from 10 to 25 minutes, or from 15 to 20 minutes.

FIG. 3 depicts an exemplary process of making a RTU phosphates solution that includes the steps of adding potassium hydrogen phosphate to water at a concentration of 1180 mg/100 ml with stirring, wherein the potassium hydrogen phosphate contains no more than 2 ppm aluminum, adding potassium dihydrogen phosphate to the water at a concentration of 1120 mg/100 ml with stirring, wherein the potassium dihydrogen phosphate contains no more than 2 ppm aluminum, and adding sodium chloride to the water at a concentration of 900 mg/100 ml with stirring, wherein the sodium chloride contains no more than 0.2 ppm aluminum, thereby forming the aqueous potassium phosphates in sodium chloride solution.

In additional or alternative embodiments, the method of making the aqueous potassium phosphates in sodium chloride solution includes filter sterilizing a fixed volume of the aqueous potassium phosphates in sodium chloride solution into a flexible container. Typically, a fixed volume of the solution is 100 ml provided to a sterile flexible container (e.g., an IV bag). With the fixed volume of the solution dispensed in the flexible container, the flexible container may be terminally sterilized. Preferably, the terminal sterilization is autoclaving to sterility. For storage and/or transport of the terminally sterilized flexible container of RTU aqueous potassium phosphates in sodium chloride solution, the flexible container may be placed inside an aluminum pouch for protective storage and transport.

In contrast to current practice where remaining concentrated phosphates solutions after withdrawal must be discarded after 24-48 hours (due to crystallization and/or precipitation issues), the inventors unexpectedly discovered that the RTU solutions could remain chemically stable and did not undergo microbial spoilage where RTU solutions were packaged and autoclaved in the package. Most typically, stability and/or concentration of the cations and anions was further promoted where the autoclaved container was packaged into a secondary container (typically containing a metal foil such as aluminum) and/or where the space between the containers was flushed with nitrogen or other inert gas to remove oxygen before sealing the secondary (overwrap) container. The inventors also observed that the type of polymer had at least some influence on storage stability and dimensional stability under autoclaving conditions.

Based on stability studies performed by the inventors, contemplated solutions can be stored for extended periods such as at least 1 week, at least 2 weeks, at least 3 weeks, at least 1 month, at least 2 months, at least 3 months, at least 6 months, at least 1 year, and even longer without significant changes in the product composition. Such storage can be performed under refrigerated conditions (e.g., 2-8° C.), at ambient conditions (e.g., 25° C., 40% relative humidity), at warm conditions (e.g., 30° C., 65% relative humidity), and even at accelerated storage conditions (e.g., 40° C., 15% relative humidity).

For example, the inventors observed that the solutions may have, after autoclaving and storage of at least 3 months at 25° C. and 40% relative humidity, a liquid particle count of no more than 400, or no more than 360, or no more than 330, or no more than 300, or no more than 170, or no more than 150, or no more than 120, or no more than 100 for particles having a size of equal to or greater than 25 micrometer size and no more than 30, or no more than 25, or no more than 20, or no more than 17, or no more than 14, or no more than 10 for particles having a size of equal to or greater than 15 micrometer size. Alternatively, or additionally, the solutions may have, after autoclaving and storage of at least 3 months at 25° C. and 40% relative humidity, a change in phosphorus and/or potassium content of no more than +/−3% (absolute), or no more than +/−2.5% (absolute), or no more than +/−2.0% (absolute), or no more than +/−1.5% (absolute), or no more than +/−1.0% (absolute), or no more than +/−0.8% (absolute), or no more than +/−0.6% (absolute), relative to initial conditions. Likewise, the solutions may have, after autoclaving and storage of at least 3 months at 25° C. and 40% relative humidity, a change in sodium and/or chloride of no more than +/−2.5% (absolute), or no more than +/−2.0% (absolute), or no more than +/−1.5% (absolute), or no more than +/−1.0% (absolute), or no more than +/−0.8% (absolute), or no more than +/−0.6% (absolute), or no more than +/−0.4% (absolute), relative to initial conditions.

Notably, the inventive RTU aqueous potassium phosphates in sodium chloride solution may be efficiently administered to a patient in need of phosphorus replacement therapy. Advantageously, the method includes easily administering the sterile ready-to-use (RTU) potassium phosphates in sodium chloride solution from the flexible container to the patient at a rate of infusion and by a route of administration corresponding to the patient's age and degree of need of phosphorus replacement. As the flexible container comprises a fixed volume (e.g., 100 ml) of the sterile RTU potassium phosphates in sodium chloride solution includes 15 mmol/100 ml Phosphorus, administration to adult or pediatric patients by peripheral venous catheter or central venous catheter may be readily accomplished based on programming the infusion rate accordingly.

In preferred embodiments, the rate of infusion of the sterile RTU potassium phosphates in sodium chloride solution into the patient is selected from 6.8 mmol/hour or 15 mmol/hour. In typical embodiments, the sterile RTU potassium phosphates in sodium chloride solution is administered to an adult or pediatric patient 12 years of age and older by peripheral venous catheter at 6.8 mmol/hour. In more preferred embodiments, the concentration of phosphates administered by peripheral venous catheter is not more than 6.8 mmol/100 ml in adult patients or pediatric patient 12 years of age and older and not more than 2.7 mmol/100 ml in pediatric patients less than 12 years of age.

In other typical embodiments, the sterile RTU potassium phosphates in sodium chloride solution is administered to an adult or pediatric patient 12 years of age and older by central venous catheter at 15 mmol/hour. In more preferred embodiments, the concentration of phosphates administered by central venous catheter is not more than 18 mmol/100 ml in adult patients or pediatric patient 12 years of age and older and not more than 5.5 mmol/100 ml in pediatric patients less than 12 years of age.

EXAMPLES

Formulation of ingredients for potassium phosphates in sodium chloride injection 15 mmol/100 ml solution. As set forth in Tables 3-4 below, exemplary amounts of potassium phosphate monobasic (potassium dihydrogen phosphate, $KH_2PO_4$), potassium phosphate dibasic (potassium hydrogen phosphate, $K_2HPO_4$) are the active pharmaceutical ingredients (API), thereby serving an active function. For a 15 mmol/100 ml concentration of phosphorus, 11.2 mg/mL $KH_2PO_4$ and 11.8 mg/mL $K_2HPO_4$ are added to water with mixing as disclosed herein. The deionized water is to volume (quantum satis (Q.S.)), which for the ready-to-use (RTU) formulation disclosed herein, is fixed at 100 ml. Sodium chloride (NaCl) is an admixture carrier and tonicity agent having a IIG limit of 0.9" weight/volume (w/v). Accordingly, for a 100 ml solution, 900 mg of NaCl is added.

Table 5 provides specifications for Monobasic Potassium Phosphate, Table 6 provides specifications for Dibasic Potassium Phosphate, Table 7 provides specifications for Sodium Chloride, and Table 8 provides specifications for Potassium Phosphates in Sodium Chloride Injection, RTU.

TABLE 3

Formulation of potassium phosphates in sodium chloride injection solution (15 mmol/100 ml of Phosphorus and 22 mEq/100 mL of Potassium)

| Active and Excipient Details | IIG Limit (mg/mL) | Function | Formulation |
|---|---|---|---|
| Potassium Phosphate monobasic | Not Applicable | Active | 11.2 mg |
| Potassium Phosphate dibasic | Not Applicable | Active | 11.8 mg |
| Sodium Chloride | 0.9% w/v | Admixture carrier | 9 mg |
| Water for Injection/ Deionized Water | Q.S. to mL | Vehicle | 100 mL |

TABLE 4

Batch formulation of potassium phosphates injection solution (15 mmol/100 ml of Phosphorus and 22 mEq/100 mL of Potassium) in 1 liter (1000 ml). Formulation for Bulk solution of Potassium Phosphates in Sodium Chloride Injection, RTU

| | Formulation Batch Size: 1000 mL | |
|---|---|---|
| Active and Excipient Details | Composition per mL | Batch Qty. per 1000 mL |
| Potassium Phosphate monobasic | 11.2 mg | 11.2 g or 11200 mg |
| Potassium Phosphate dibasic | 11.8 mg | 11.8 g or 11800 mg |
| Sodium Chloride | 9 mg | 9 g or 9000 mg |
| Water for Injection/Deionized Water | 1 mL | 1000 mL |

TABLE 5

Specification of Monobasic Potassium Phosphate API

| Sr.No. | Test | Specification | Reference |
|---|---|---|---|
| 1. | Description | Colorless crystals or white, granular or crystalline powder | USP |
| 2. | Solubility | Freely soluble in water; practically insoluble in alcohol | USP |

TABLE 5-continued

Specification of Monobasic Potassium Phosphate API

| Sr.No. | Test | Specification | Reference |
|---|---|---|---|
| 3. | | Identification tests | |
| 3.1. | Potassium | Meet the requirement | USP <191> |
| 3.2. | Phosphate | Meet the requirement | USP <191> |
| 4. | LOD@105° C. | Not more than 1.0% | USP monograph |
| 5. | Assay | Not less than 98.0% and Not more than 100.5% on the dried basis | USP monograph |
| 6. | Insoluble substances | Not more than 0.2% (NMT 20 mg) | USP monograph |
| 7. | | Impurities | |
| 7.1. | Arsenic | Not more than 3 ppm (NMT 3 µg/g) | USP <211>, Method I |
| 7.2. | Lead | Not more than 5 ppm (NMT 5 µg/g) | USP <251> |
| 7.3. | Limit of Fluoride | Not more than 0.001% (NMT 10 µg/g) | USP monograph |
| 8. | Aluminum content | Not more than 2 ppm | In-House |
| 9. | Bacterial Endotoxin | Not more than 0.1 EU/mg of Monobasic Potassium phosphate | USP <85> |
| 10. | | Microbial Enumeration Tests | |
| | Total Aerobic Microbial Count (TAMC) | Not more than 1000 cfu/g | USP <61> & <1111> |
| | Total Combined Yeasts and Molds Count (TYMC) | Not more than 100 cfu/g | |
| 11. | Total Coliforms | Negative | USP <62> & <1111> |
| 12. | Residual Solvents | Meets the requirement | USP |

TABLE 6

Specification of Dibasic Potassium Phosphate API

| Sr. No. | Test | Specification | Reference |
|---|---|---|---|
| 1. | Description | Colorless or white, somewhat hygroscopic, granular powder. | USP |
| 2. | Solubility | Freely soluble in water; very slightly soluble in alcohol. | USP |
| 3. | | Identification tests | |
| 3.1. | Potassium | Meet the requirement | USP <191> |
| 3.2. | Phosphate | Meet the requirement | USP <191> |
| 4. | LOD@105° C. | 1.0% of its weight. | USP <731> |
| 5. | pH (5%) | 8.5-9.6 | USP <791> |
| 6. | Assay | Not less than 98.0% and Not more than 100.5% on the dried basis | USP monograph |
| 7. | | Impurities | |
| 7.1. | Insoluble substances | The weight of the residue is Not more than 20 mg (Not more than 0.2%). | USP monograph |
| 7.2. | Carbonate | NMT a few bubbles are evolved. | USP monograph |
| 7.3. | Chloride and Sulfate, Chloride | Shows no more chloride than corresponds to 0.40 mL of 0.020 N hydrochloric acid (Not more than 0.03%) | USP <221> |
| 7.4. | Chloride and Sulfate, Sulfate | Shows no more sulfate than corresponds to 0.20 mL of 0.020 N sulfuric acid (Not more than 0.1%) | USP <221> |
| 7.5. | Arsenic | Not more than 3 ppm (3 µg/g) | USP <211>, Method I |
| 7.6. | Iron | Any red color produced within 1 h is not darker than that of a control prepared from 1 mL of Standard Iron Solution: Not more than 30 ppm (0.003%) | USP <241> |
| 7.7. | Sodium | A solution (1 in 10) tested on a platinum wire imparts no pronounced yellow color to a nonluminous flame. | USP monograph |
| 7.8. | Limit of Fluoride | Not more than 0.001% (10 µg/g) | USP monograph |
| 7.9. | Limit of Monobasic/Tribasic salt | A blue color is produced, which is changed to yellow (with a greenish tinge) by the addition of NMT 0.4 mL of 1 N hydrochloric acid. | USP monograph |
| 8. | Aluminum content | Not more than 2 ppm | In-House |
| 9. | Bacterial Endotoxin | Not more than 0.1 EU/mg of Dibasic Potassium phosphate | USP <85> |
| | | Microbial Enumeration Tests | |
| 10. | Total Aerobic Microbial Count (TAMC) | Not more than 1000 cfu/g | USP <61> & <1111> |
| | Total Combined Yeasts and Molds Count (TYMC) | Not more than 100 cfu/g | |
| 11. | Total Coliforms | Negative | USP <62> & <1111> |
| 12. | Residual Solvents | Meets the requirement | USP |

TABLE 7

Specification of Sodium Chloride

| Sr. No. | Test | Specification | Reference |
|---|---|---|---|
| 1. | Description | Colorless, cubic crystals or white crystalline powder. Has a saline taste | USP |
| 2. | Solubility | Freely soluble in water; soluble in glycerin; slightly soluble in alcohol | USP |
| 3. | | Identification tests | |
| 3.1. | Sodium | Meet the requirement | USP <191> |
| 3.2. | Chloride | Meet the requirement | USP <191> |
| 4. | LOD@105° C. | 0.5% of its weight. | USP <731> |
| 5. | Assay | Not less than 99.0% and Not more than 100.5% on the dried basis | USP monograph |
| 6. | Appearance of Solution | Meet the requirement | USP monograph |
| 7. | Acidity or Alkalinity | Meet the requirement | USP monograph |
| 8. | | Impurities | |
| 8.1. | Aluminum (Al) | Not more than 0.2 ppm | USP monograph |
| 8.2. | Arsenic | Not more than 1 ppm | USP <211>, Method 1 |
| 8.3. | Barium | Should be complies | USP monograph |
| 8.4. | Ferrocyanide | Should be complies | USP monograph |
| 8.5. | Iodide | Should be complies | USP monograph |
| 8.6. | Iron | Not more than 2 ppm | USP monograph |
| 8.7. | Bromides | Not more than 100 ppm | USP monograph |
| 8.8. | Phosphates | Not more than 25 ppm | USP monograph |
| 8.9. | Potassium | Not more than 500 ppm | USP monograph |
| 8.10. | Magnesium and Alkaline Earth Metals (as Ca) | Not more than 100 ppm | USP monograph |
| 8.11. | Nitrite (Absorbance Value) | Not more than 0.01% | USP monograph |
| 8.12. | Sulfate | Not more than 200 ppm | USP monograph |
| 9. | Sterility | Meets the requirement | USP <71> |
| 10. | Bacterial Endotoxin | Not more than 0.1 EU/mg of Dibasic Potassium phosphate | USP <85> |
| 11. | Residual Solvents | Meets the requirement | USP |

TABLE 8

Specification of Potassium Phosphates in Sodium Chloride Injection, RTU

| Sr. No. | Test | Release Specification | Shelf Life Specification | Reference |
|---|---|---|---|---|
| 1. | Description | clear colorless solution, free from visible particles | clear colorless solution, free from visible particles | In-House |
| 2. | | Identification tests | | |
| 7.1 | Potassium | Meet the requirement | Not Applicable | USP <191> |
| 7.2 | Phosphate | Meet the requirement | Not Applicable | USP <191> |
| 7.3 | Sodium | Meet the requirement | Not Applicable | USP <191> |
| 7.4 | Chloride | Meet the requirement | Not Applicable | USP <191> |
| 3. | pH | Between 6.0 and 7.0 | Between 6.0 and 7.0 | In-House |
| 4. | Osmolality | 550-700 mOsmol/kg | 550-700 mOsmol/kg | USP <785> |
| 5. | Aluminum content | Not more than 50 µg/L | Not more than 50 µg/L | In-house |
| 6. | | Particulate matter | | |
| 3.1 | | A) Visible particles | | USP <790> |
| | Visual inspection | Should be free of visible particles | Should be free of visible particles | |
| 3.2 | | B) Sub-visible Particles (By Light Obscuration method) | | USP <788>, Method-I; B |
| | 10 µm size particles | Not more than 6000 particles per container | Not more than 6000 particles per container | |
| | 25 µm size particles | Not more than 600 particles per container | Not more than 600 particles per container | |
| 7. | Container content for Injections | Not less than 100.0 mL | Not less than 100.0 mL | USP <697> |
| 8. | Assay of Potassium (Label Claim: Each 100 mL bag contains 8.50 mg/mL of Potassium | Not less than 95.0% and Not more than 105.0% | Not less than 90.0% and Not more than 110.0% | In-house |
| 9. | Assay of Phosphorus (Label Claim: Each 100 mL bag contains 4.65 mg/mL of Phosphorus) | Not less than 95.0% and Not more than 105.0% | Not less than 90.0% and Not more than 110.0% | In-house |
| 10. | Assay of Sodium (Label Claim: Each 100 mL bag contains 3.57 mg/mL of Sodium) | Not less than 95.0% and Not more than 105.0% | Not less than 90.0% and Not more than 110.0% | In-house |

TABLE 8-continued

Specification of Potassium Phosphates in Sodium Chloride Injection, RTU

| Sr. No. | Test | Release Specification | Shelf Life Specification | Reference |
|---|---|---|---|---|
| 11. | Assay of Chloride (Label Claim: Each 100 mL bag contains 5.43 mg/mL of Chloride) | Not less than 95.0% and Not more than 105.0% | Not less than 90.0% and Not more than 110.0% | In-house |
| 12. | Sterility | Meets the requirement | Meets the requirement | USP <71> |
| 13. | Bacterial endotoxins | Not more than 1.10 USP EU/mg | Not more than 1.10 USP EU/mg | USP <85> |
| 14. | Residual Solvents | Meets the requirement | Not Applicable | USP <467> (Option 1) |
| 15. | Container Closure integrity test | Meets the requirement | Meets the requirement | USP <1207.2> |

Ion Chromatography Methods:

Assay of Anions (Phosphorus and Chloride) and Cations (Potassium and Sodium) By Ion Chromatography: All the solution preparations (Mobile Phase, Standard, Sample) should be prepared in plastic ware (Volumetric flask, beakers, pipette tips, eluent bottles, etc.).

Preparation of Mobile Phases:

Mobile Phase for Anions (9 mM Na2CO3): Take 18.0 mL of Dionex Sodium Carbonate concentrate (0.5M) and dilute to 1000 mL with IC grade water (18.2 MΩ·cm, 0.22 μm filtered), mixed well and degas it for 10 minutes. Purge the solution with helium at 8-10 psi for 10 minutes. After purging blanket/pressurize the container with helium at 8-10 psi for 10 minutes.

Mobile Phase for Cations (20 mm Methanesulfonic Acid (MSA)): Take 50.0 mL of Dionex CS12A Eluent concentrate (0.4M Methanesulfonic Acid) and dilute to 1000 mL with IC grade water (18.2 MΩ·cm, 0.22 μm filtered), mixed well and degas it for 10 minutes.

Diluent: Use IC grade water (18.2 MΩ·cm, 0.22 μm filtered) as Diluent.

IC Conditions: The liquid chromatography equipped with conductivity detector, an injector and a data processor.

Chromatographic Conditions for Anions are shown in Table 9.

TABLE 9

| Parameters | Conditions |
|---|---|
| Guard Column | Dionex IonPac RFIC AG9-HC (2 × 50 mm) |
| Column | Dionex IonPac RFIC AS9-HC (2 × 250 mm) |
| Flow rate | 0.4 mL/min. |
| Detector | Suppressed conductivity |
| Injection volume | 50 μL |
| Run time | 15 Minutes |
| Cell Temperature | 30° C. |
| Sample Cooler Temp. | 25° C. |
| Suppressor | AERS 500e 2 mm (constant voltage & recycle mode) (18 mA) |

Chromatographic Conditions for Anions are shown in Table 10.

TABLE 10

| Parameters | Conditions |
|---|---|
| Guard Column | Dionex IonPac RFIC CG12A (4 × 50 mm) |
| Column | Dionex IonPac RFIC CS12A (4 × 250 mm) |
| Flow rate | 0.7 mL/min. |
| Detector | Suppressed conductivity |
| Injection volume | 50 μL |
| Run time | 15 Minutes |
| Cell Temperature | 30° C. |
| Sample Cooler Temp. | 25° C. |
| Suppressor | CDRS 600 4 mm (constant voltage & recycle mode) (41 mA) |

Preparation of Analytical Solutions:

Preparation of Standard Solution-1 Set-1 (For Anions): Transfer 0.465 mL of Phosphate Phosphorus Standard Solution for IC and 0.543 mL of Chloride Standard Solution for IC into 25 mL of plastic volumetric flask made up to the mark with diluent, mixed well. Further diluted 5.0 mL above solution into 25 mL of plastic volumetric flask made up to the mark with diluent, mixed well. (This solution contains 3.720 μg/mL of Phosphorus and 4.344 μg/mL of Chloride).

Preparation of Standard Solution-1 Set-2 (For Anions): Transfer 0.465 mL of Phosphate Phosphorus Standard Solution for IC and 0.543 mL of Chloride Standard Solution for IC into 25 mL of plastic volumetric flask made up to the mark with diluent, mixed well. Further diluted 5.0 mL above solution into 25 mL of plastic volumetric flask made up to the mark with diluent, mixed well. (This solution contains 3.720 μg/mL of Phosphorus and 4.344 μg/mL of Chloride).

Preparation of Standard solution-2 Set-1 (For Cations): Transfer 0.850 mL of Potassium Standard Solution for IC and 0.357 mL of Sodium Standard Solution for IC into 25 mL of plastic volumetric flask made up to the mark with diluent, mixed well. Further diluted 5.0 mL above solution into 25 mL of plastic volumetric flask made up to the mark with diluent, mixed well. (This solution contains 6.800 μg/mL of Potassium and 2.856 μg/mL of Sodium).

Preparation of Standard solution-2 Set-2 (For Cations): Transfer 0.850 mL of Potassium Standard Solution for IC and 0.357 mL of Sodium Standard Solution for IC into 25 mL of plastic volumetric flask made up to the mark with diluent, mixed well. Further diluted 5.0 mL above solution into 25 mL of plastic volumetric flask made up to the mark with diluent, mixed well. (This solution contains 6.800 μg/mL of Potassium and 2.856 μg/mL of Sodium).

Preparation of Sample Solution: Transfer 1.0 mL of Finished Product into 100 mL of plastic volumetric flask made up to the mark with diluent, mixed well. Further diluted 4.0 mL above solution into 50 mL of plastic volumetric flask made up to the mark with diluent, mixed well. (This solution contains 3.720 μg/mL of Phosphorus, 4.344 μg/mL of Chloride, 6.800 μg/mL of Potassium and 2.856 μg/mL of Sodium).

Injection Sequence for Anions is shown in Table 11:

TABLE 11

| Sr. No. | Solution Name | Number of Injection |
|---|---|---|
| 1. | Column Condition | 3 |
| 2. | Diluent | 1 |
| 3. | Standard Solution-1 Set-1 (For Anions) | 6 |
| 4. | Standard Solution-1 Set-2 (For Anions) | 2 |
| 5. | Diluent | 1 |
| 6. | Sample Solution-1 to 6 | 2 |
| 7. | Diluent | 1 |
| 8. | Bracketing Standard Solution-1 Set-1 (For Anions) | 1 (Inject after 6 Test Samples) |

Injection Sequence for Anions is shown in Table 12:

TABLE 12

| Sr. No. | Solution Name | Number of Injection |
|---|---|---|
| 1. | Column Condition | 3 |
| 2. | Diluent | 1 |
| 3. | Standard Solution-2 Set-1 (For Cations) | 6 |
| 4. | Standard Solution-2 Set-2 (For Cations) | 2 |
| 5. | Diluent | 1 |
| 6. | Sample Solution-1 to 6 | 2 |
| 7. | Diluent | 1 |
| 8. | Bracketing Standard Solution-2 Set-1 (For Cations) | 1 (Inject after 6 Test Samples) |

System Suitability Requirements are shown in Table 13:

| Parameter | Phosphorus Peak | Chloride Peak | Potassium Peak | Sodium Peak |
|---|---|---|---|---|
| % Correlation between Standard Solution Set-1 and Set-2 | No Less Than 98.0 and No More Than 102.0 | | | |
| % RSD of Standard | No More Than 2.0 | | | |
| USP tailing of standard | No More Than 2.0 | | | |
| USP plate count of standard | No More Than 2000 | | | |
| Overall % RSD of Standard | No More Than 2.0 | | | |

Calculate the % correlation in standard solution and report the value. If any peak response identified in Diluent at principal peaks then mean the peak response of each individual principal peak from all the diluent injected in sequence and subtract that individual peak response from Standard and Sample respectively.

% Correlation between Standard Solution Set-1 and Set-2 is calculated as $$\frac{Rstd\,2}{Rstd\,1} \times \frac{Vstd\,1}{Vstd\,2} \times 100$$

Where Rstd 1 is Average Peak area of each individual peak in Standard Solution Set-1, Rstd 2 is Average Peak area of each individual peak in Standard Solution Set-2, Vstd 1 is Dilution of Standard Solution Set-1, and Vstd 2 is Dilution of Standard Solution Set-2.

Calculations

Calculate the Assay in test solution and report the value.
Note: If any peak response identified in Diluent at principal peaks then mean the peak response of each individual principal peak from all the diluent injected in sequence and subtract that individual peak response from Standard and Sample respectively.

% Assay is calculated as follows:

$$\frac{Ru}{Rs} \times \frac{Vs}{25} \times \frac{5.0}{25} \times \frac{100}{Vt} \times \frac{50}{4.0} \times \frac{P}{L.C.}$$

Where Ru is Average Peak area of each individual peak in Sample Solution, Rs is Average Peak area of each individual peak in Standard Solution Set-1, Vs is Volume of each Anion Standards (Phosphorus and Chloride) and Cation Standards (Potassium and Sodium) (in mL), Vt is Volume of Sample Solution (in mL), P is Potency of each individual Standard, and L.C. is Label Claim of each Anions and Cations as follows: Phosphorus (Anion)—4.65 mg/mL, Chloride (Anion)—5.43 mg/mL, Potassium (Cation)—8.50 mg/mL, and Sodium (Cation)—3.57 mg/mL.

Figure 4:
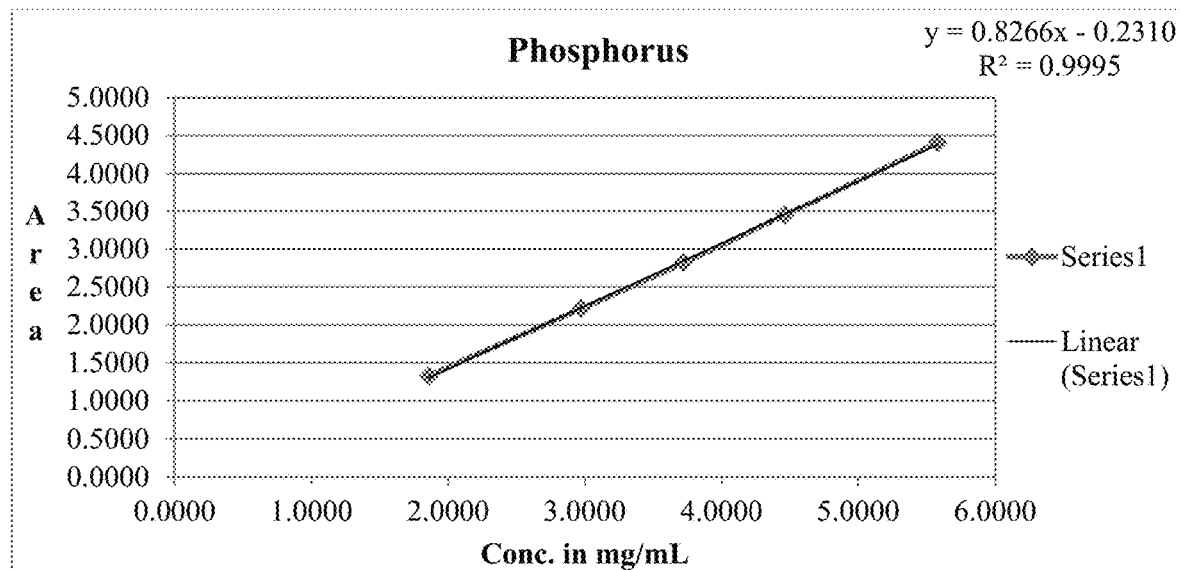
FIG. 4 is an exemplary linearity curve for determination of phosphorus using ion chromatography.
Figure 5:
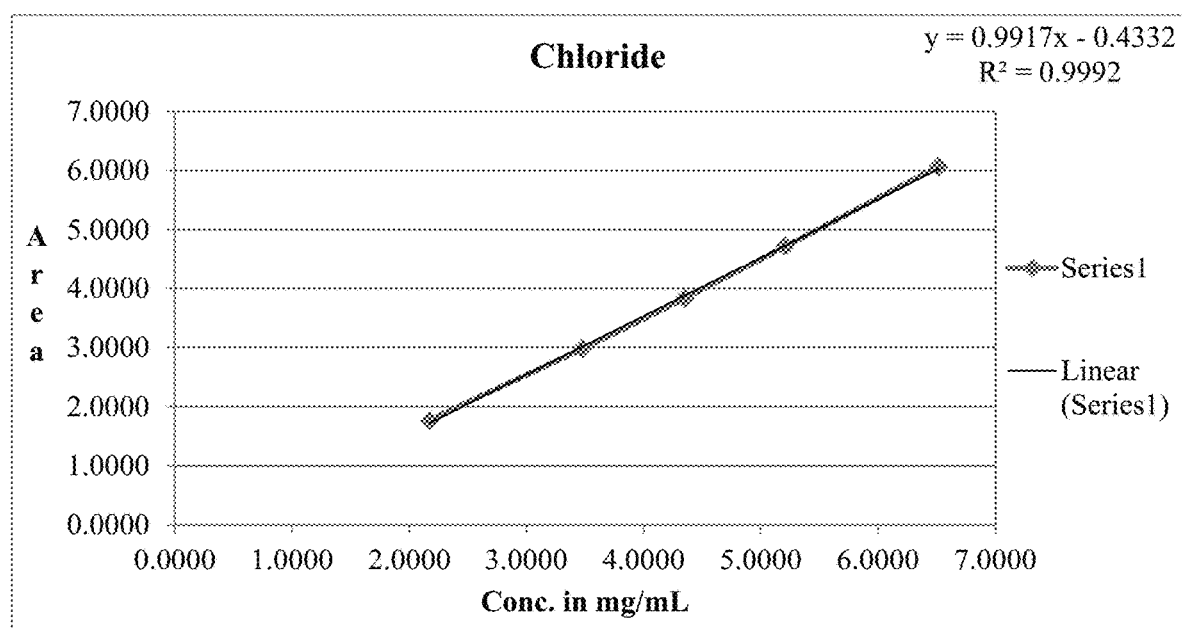
FIG. 5 is an exemplary linearity curve for determination of chloride using ion chromatography.
Figure 6:
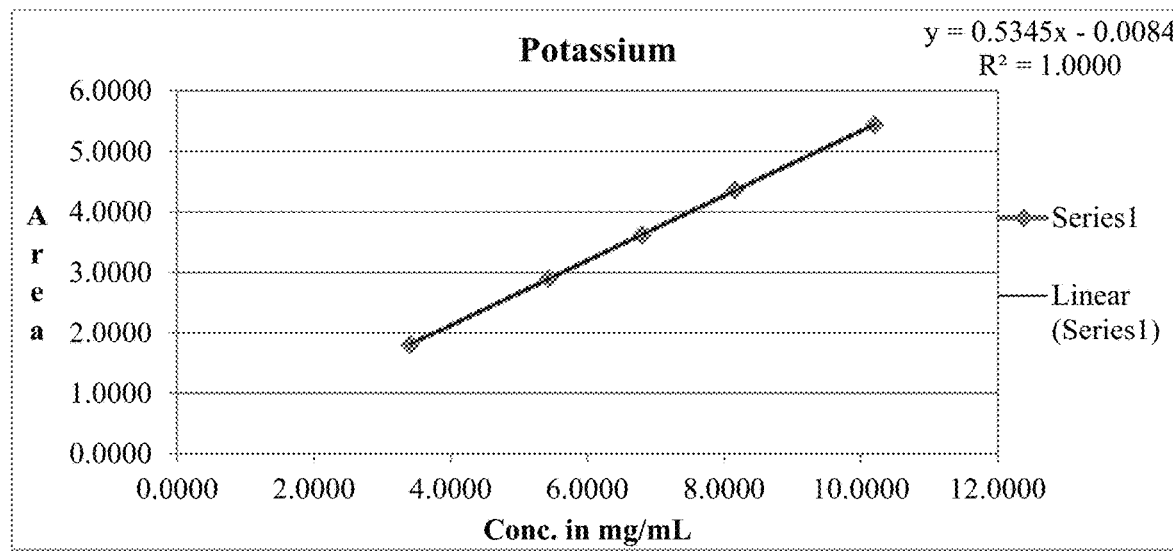
FIG. 6 is an exemplary linearity curve for determination of potassium using ion chromatography.
Figure 7:
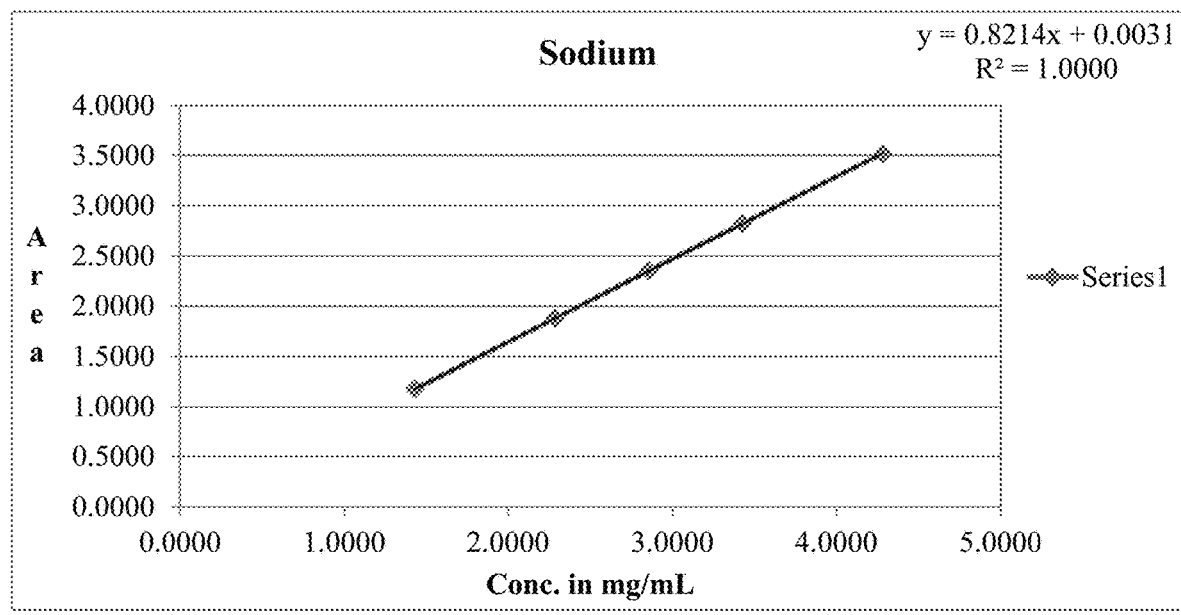
FIG. 7 is an exemplary linearity curve for determination of sodium using ion chromatography.

Validation for Ion Chromatography:

The Ion Chromatographic process was then tested and validated, and exemplary results are shown in FIGS. 4-7 depicting excellent linearity in the relevant range for the various ions. More specifically, FIG. 4 depicts the linearity curve for phosphorus, FIG. 5 depicts the linearity curve for chloride, FIG. 6 depicts the linearity curve for potassium, and FIG. 7 depicts the linearity curve for sodium, and Table 13 provides exemplary results from these linearity curves.

TABLE 13

| | Anions | | Cations | |
|---|---|---|---|---|
| Name | Phosphorus | Chloride | Potassium | Sodium |
| Correlation coefficient | 0.9998 | 0.9996 | 1.0000 | 1.0000 |
| $R^2$ Value | 0.9995 | 0.9992 | 1.0000 | 1.0000 |
| Slope of regression line | 0.8266 | 0.9917 | 0.5345 | 0.8214 |
| Y intercept | −0.2310 | −0.4332 | −0.0084 | 0.0031 |

Tables 14-17 provide further data for the accuracies for phosphorus (Table 14), chloride (Table 15), potassium (Table 16), and sodium (Table 17).

TABLE 14

| Sr No. | Sample name | Amount added | Amount recovered | % Recovery |
|---|---|---|---|---|
| 1 | Accuracy Level-50% Set-1 | 2.3483 | 2.3752 | 101.1 |
| 2 | Accuracy Level-50% Set-2 | 2.3489 | 2.3674 | 100.8 |
| 3 | Accuracy Level-50% Set-3 | 2.3513 | 2.3592 | 100.3 |
| | Mean | | | 100.7 |
| | STD Dev | | | 0.4 |
| | % RSD | | | 0.4 |
| 1 | Accuracy Level-100% Set-1 | 4.6924 | 4.6986 | 100.1 |
| 2 | Accuracy Level-100% Set-2 | 4.6967 | 4.7287 | 100.7 |
| 3 | Accuracy Level-100% Set-3 | 4.6987 | 4.7609 | 101.3 |
| | Mean | | | 100.7 |
| | STD Dev | | | 0.6 |
| | % RSD | | | 0.6 |
| 1 | Accuracy Level-150% Set-1 | 7.0437 | 7.0506 | 100.1 |
| 2 | Accuracy Level-150% Set-2 | 7.0428 | 7.0125 | 99.6 |
| 3 | Accuracy Level-150% Set-3 | 7.0436 | 7.0702 | 100.4 |
| | Mean | | | 100.0 |
| | STD Dev | | | 0.4 |
| | % RSD | | | 0.4 |

TABLE 15

| Sr No. | Sample name | Amount added | Amount recovered | % Recovery |
|---|---|---|---|---|
| 1 | Accuracy Level-50% Set-1 | 2.7056 | 2.7676 | 102.3 |
| 2 | Accuracy Level-50% Set-2 | 2.7079 | 2.7514 | 101.6 |
| 3 | Accuracy Level-50% Set-3 | 2.7050 | 2.7540 | 101.8 |
|  | Mean |  |  | 102.0 |
|  | STD Dev |  |  | 0.5 |
|  | % RSD |  |  | 0.5 |
| 1 | Accuracy Level-100% Set-1 | 5.4170 | 5.5163 | 101.8 |
| 2 | Accuracy Level-100% Set-2 | 5.4148 | 5.5327 | 102.2 |
| 3 | Accuracy Level-100% Set-3 | 5.4067 | 5.5532 | 102.7 |
|  | Mean |  |  | 102.0 |
|  | STD Dev |  |  | 0.3 |
|  | % RSD |  |  | 0.3 |
| 1 | Accuracy Level-150% Set-1 | 8.1173 | 8.2750 | 101.9 |
| 2 | Accuracy Level-150% Set-2 | 8.1221 | 8.2221 | 101.2 |
| 3 | Accuracy Level-150% Set-3 | 8.1206 | 8.2802 | 102.0 |
|  | Mean |  |  | 101.7 |
|  | STD Dev |  |  | 0.4 |
|  | % RSD |  |  | 0.4 |

TABLE 16

| Sr No. | Sample name | Amount added | Amount recovered | % Recovery |
|---|---|---|---|---|
| 1 | Accuracy Level-50% Set-1 | 4.2860 | 4.2825 | 99.9 |
| 2 | Accuracy Level-50% Set-2 | 4.2890 | 4.2816 | 99.8 |
| 3 | Accuracy Level-50% Set-3 | 4.2875 | 4.2808 | 99.8 |
|  | Mean |  |  | 99.8 |
|  | STD Dev |  |  | 0.1 |
|  | % RSD |  |  | 0.1 |
| 1 | Accuracy Level-100% Set-1 | 8.5660 | 8.5052 | 99.3 |
| 2 | Accuracy Level-100% Set-2 | 8.5716 | 8.5544 | 99.8 |
| 3 | Accuracy Level-100% Set-3 | 8.5774 | 8.6057 | 100.3 |
|  | Mean |  |  | 99.8 |
|  | STD Dev |  |  | 0.5 |
|  | % RSD |  |  | 0.5 |
| 1 | Accuracy Level-150% Set-1 | 12.8574 | 12.8679 | 100.1 |
| 2 | Accuracy Level-150% Set-2 | 12.8568 | 12.7590 | 99.2 |
| 3 | Accuracy Level-150% Set-3 | 12.8577 | 12.8449 | 99.9 |
|  | Mean |  |  | 99.7 |
|  | STD Dev |  |  | 0.5 |
|  | % RSD |  |  | 0.5 |

TABLE 17

| Sr No. | Sample name | Amount added | Amount recovered | % Recovery |
|---|---|---|---|---|
| 1 | Accuracy Level-50% Set-1 | 1.7779 | 1.7785 | 100.0 |
| 2 | Accuracy Level-50% Set-2 | 1.7795 | 1.7730 | 99.6 |
| 3 | Accuracy Level-50% Set-3 | 1.7776 | 1.7744 | 99.8 |
|  | Mean |  |  | 99.8 |
|  | STD Dev |  |  | 0.3 |
|  | % RSD |  |  | 0.3 |
| 1 | Accuracy Level-100% Set-1 | 3.5597 | 3.5414 | 99.5 |
| 2 | Accuracy Level-100% Set-2 | 3.5583 | 3.5502 | 99.8 |
| 3 | Accuracy Level-100% Set-3 | 3.5530 | 3.5647 | 100.3 |
|  | Mean |  |  | 99.7 |
|  | STD Dev |  |  | 0.2 |
|  | % RSD |  |  | 0.2 |
| 1 | Accuracy Level-150% Set-1 | 5.3342 | 5.3404 | 100.1 |
| 2 | Accuracy Level-150% Set-2 | 5.3374 | 5.3049 | 99.4 |
| 3 | Accuracy Level-150% Set-3 | 5.3364 | 5.3340 | 100.0 |
|  | Mean |  |  | 99.8 |
|  | STD Dev |  |  | 0.4 |
|  | % RSD |  |  | 0.4 |

TABLE 18

| Ions | Recovery Levels | Mean % Recovery | % RSD |
|---|---|---|---|
| Phosphorus | 50% Level | 100.7 | 0.4 |
|  | 100% Level | 100.7 | 0.6 |
|  | 150% Level | 100.0 | 0.4 |
| Chloride | 50% Level | 102.0 | 0.5 |
|  | 100% Level | 102.0 | 0.3 |
|  | 150% Level | 101.7 | 0.4 |
| Potassium | 50% Level | 99.8 | 0.1 |
|  | 100% Level | 99.8 | 0.5 |
|  | 150% Level | 99.7 | 0.5 |
| Sodium | 50% Level | 99.8 | 0.3 |
|  | 100% Level | 99.7 | 0.2 |
|  | 150% Level | 99.8 | 0.4 |

In conclusion, it should therefore be appreciated that the above test method established that the method is specific, linear, accurate, precise, robust and stable. Based on solution stability data (data not shown), it was concluded that standard solution are stable up to 168 Hrs at room temperature, that sample solutions are stable up to 168 Hrs at room temperature, and that mobile phases were stable up to 72 Hrs at room temperature under continuous chromatographic conditions.

Aluminum Detection

Figure 8:
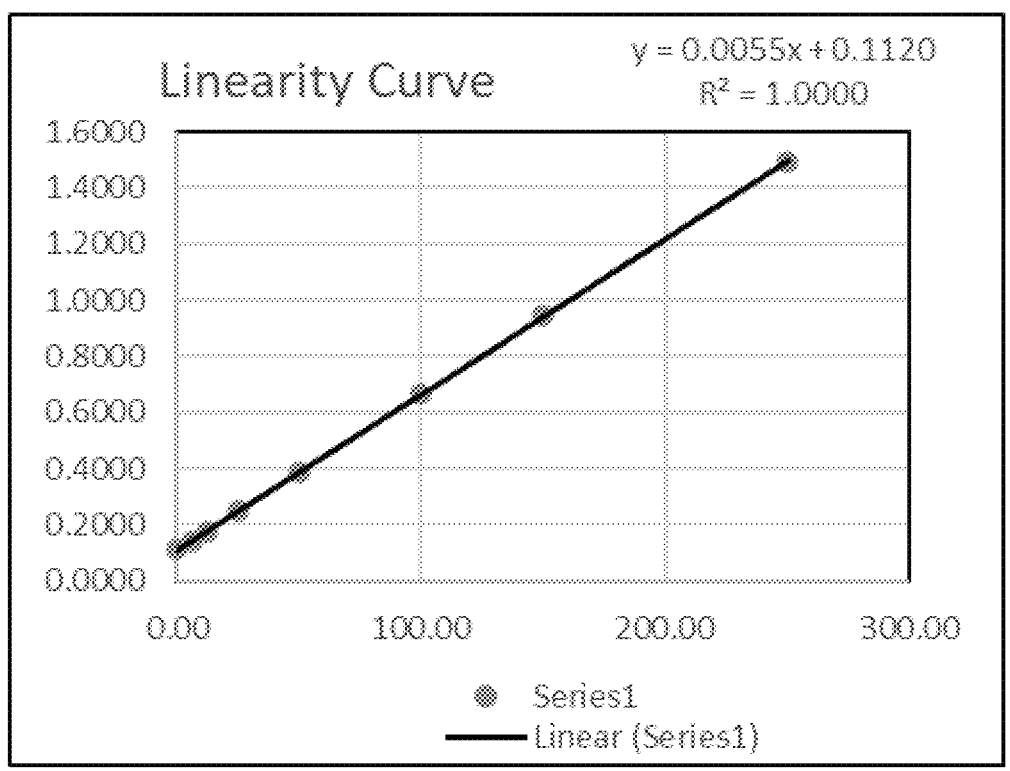
FIG. 8 is an exemplary linearity curve for determination of aluminum using Inductively Coupled Plasma Mass Spectrometry (ICP-MS).

In a similar manner, the inventors set further out to detect and quantify aluminum levels in the solutions presented herein, and FIG. 8 depicts an exemplary linearity curve for aluminum in the potassium phosphates solutions presented herein. Table 19 provides exemplary results for Accuracy & Method Precision at 100% Spiked Level by Inductively Coupled Plasma Mass Spectrometry (ICP-MS).

TABLE 19

Accuracy & Method Precision @ 100% Spiked Level

| Sets/Levels | % Recovery | Average % Recovery | AVG. | SD | % RSD |
|---|---|---|---|---|---|
| LOQ_25%_Set-1 | 113.84 | 113.92 | 105.75 | 9.8281 | 9.3 |
|  | 113.99 |  |  |  |  |
| LOQ_25%_Set-2 | 109.62 | 110.06 |  |  |  |
|  | 110.50 |  |  |  |  |
| LOQ_25%_Set-3 | 93.04 | 93.26 |  |  |  |
|  | 93.48 |  |  |  |  |
| 50%_Set-1 | 104.27 | 103.36 | 104.44 | 3.5114 | 3.4 |
|  | 102.45 |  |  |  |  |
| 50%_Set-2 | 101.87 | 101.25 |  |  |  |
|  | 100.63 |  |  |  |  |
| 50%_Set-3 | 108.41 | 108.70 |  |  |  |
|  | 108.99 |  |  |  |  |
| 100%_Set-1 | 99.52 | 99.77 | 99.76 | 4.5208 | 4.5 |
|  | 100.02 |  |  |  |  |
| 100%_Set-2 | 99.66 | 100.01 |  |  |  |
|  | 100.35 |  |  |  |  |
| 100%_Set-3 | 95.48 | 96.02 |  |  |  |
|  | 96.57 |  |  |  |  |
| 100%_Set-4 | 99.33 | 100.35 |  |  |  |
|  | 101.37 |  |  |  |  |
| 100%_Set-5 | 107.55 | 107.97 |  |  |  |
|  | 108.39 |  |  |  |  |
| 100%_Set-6 | 93.73 | 94.42 |  |  |  |
|  | 95.12 |  |  |  |  |
| 200%_Set-1 | 99.74 | 99.67 | 97.29 | 2.9961 | 3.1 |
|  | 99.59 |  |  |  |  |
| 200%_Set-2 | 99.59 | 98.53 |  |  |  |
|  | 97.47 |  |  |  |  |
| 200%_Set-3 | 94.70 | 93.68 |  |  |  |
|  | 92.65 |  |  |  |  |
| 400%_Set-1 | 96.32 | 96.07 | 95.77 | 0.3961 | 0.4 |
|  | 95.82 |  |  |  |  |
| 400%_Set-2 | 95.55 | 95.38 |  |  |  |
|  | 95.21 |  |  |  |  |

TABLE 19-continued

Accuracy & Method Precision @ 100% Spiked Level

| Sets/Levels | % Recovery | Average % Recovery | AVG. | SD | % RSD |
|---|---|---|---|---|---|
| 400%_Set-3 | 96.08<br>95.65 | 95.87 | | | |

Stability Studies

For the stability studies, the inventors investigated stability of a phosphorus solution containing saline that was prepared according to FIG. 3 from water and potassium dihydrogen phosphate ($KH_2PO_4$), potassium hydrogen phosphate ($K_2HPO_4$), and sodium chloride (NaCl), wherein the potassium dihydrogen phosphate was present in the solution an amount of about 1,120 mg/100 ml (8.2 mmol/100 ml), wherein the potassium hydrogen phosphate was present in the solution in an amount of about 1,180 mg/100 ml (6.8 mmol/100 ml), and wherein the sodium chloride was present in the solution in an amount of about 900 mg/100 ml. Thus, the solution contained 15 mmol/100 ml phosphorus (0.15 mmol/mL), 22 mEq/100 mL potassium, and had an aluminum content of about 30 mcg/L. Table 20 provides an overview of the packaging materials used and filling/autoclaving conditions employed.

TABLE 20

Potassium Phosphates in Sodium Chloride Injection
(15 mmol/100 mL of Phosphorus and 22 mEq/100 mL of Potassium)
Secondary packaging for all samples was an aluminum pouch (PET/ALU/PET/PP) and bag fill volume was 100 mL

| Bag Source | Bag Film Material | Bag Material | Bag Injection Port | Bag Injection Port material | Bag Tube Material | Batch No. (Stability Batches and Results) | Sterilization Method |
|---|---|---|---|---|---|---|---|
| TechnoFlex | PP Film/Layflat Inerta 103 (0.20-NCT) | PP | 1 | Twist off Port 823-PP INERTA016 | PP-4618 Ø 6.15 × 8.2 Tube-NCT | NPO2052 (6 Months) | Terminal Sterilization (121° C. for 15 Minutes) |
| | | | | | | NPO2092 (6 Months) | Terminal Sterilization (121° C. for 15 Minutes) |
| | | | | | | NPO21001 (6 Months) | Aseptic Filling, Terminal Sterilization (121° C. for 15 Minutes), Terminal Sterilization (115° C. for 20 Minutes) |
| TechnoFlex | PP Film/Layflat Inerta 103 (0.20-NCT) | PP | 2 | Twist off Port 823-PP INERTA016 and Injection Port | PP-4618 Ø 6.15 × 8.2 Tube-NCT | NPO2052 (6 Months), NPO2092 (6 Months) | Terminal Sterilization (121° C. for 15 Minutes) |
| TechnoFlex | PVC/Layflat MediPack-3222 (0.32-NCT) | PVC | 2 | Twist off 450 Welded PVC 3222 and Injection Port | PVC-3227 Ø 6.15 × 8.2 Tube-NCT | NPO2052 (6 Months) | Terminal Sterilization (121° C. for 15 Minutes) |
| Grifols | Not Available | PP | 1 | PP Plug for Twist off | Not Available | NPO2052 (6 Months), NPO2092 (6 Months) | Terminal Sterilization (121° C. for 15 Minutes) |
| Bausch | APP 114S 200 μm Film 160 mm Width | PP | 2 | PP Plug for Twist off and Injection Port | APP 107 Tubing Ø 8.2 × 6.2 | NPO2052 (6 Months) | Terminal Sterilization (121° C. for 15 Minutes) |
| HaemoPharm | NEXCEL M312A Film (Sealed Air) 135 × 0.40 | Polyolefins | 1 | PP Plug for Twist off in Melitek | Raumedic Tube Ø 6.2 × 8.3 | NPO21001 (6 Months) | Aseptic Filling, Terminal Sterilization (121° C. for 15 Minutes), Terminal Sterilization (115° C. for 20 Minutes) |
| | | | | | | B#192073_11 (6 Months) | Terminal Sterilization (121° C. for 15 Minutes) |
| HaemoPharm | NEXCEL M312 Film (Sealed Air) 135 × 0.40 | Polyolefins | 1 | PP Plug for Twist off in Melitek | Raumedic Tube Ø 6.2 × 8.3 | NPO21006 (6 Months) | Aseptic Filling, Terminal Sterilization (121° C. for 15 Minutes) |

TABLE 20-continued

Potassium Phosphates in Sodium Chloride Injection
(15 mmol/100 mL of Phosphorus and 22 mEq/100 mL of Potassium)
Secondary packaging for all samples was an aluminum pouch (PET/ALU/PET/PP) and bag fill volume was 100 mL

| Bag Source | Bag Film Material | Bag Material | Bag Injection Port | Bag Injection Port material | Bag Tube Material | Batch No. (Stability Batches and Results) | Sterilization Method |
|---|---|---|---|---|---|---|---|
| | | | | | | NPO21007 (6 Months) | Aseptic Filling, Terminal Sterilization (121° C. for 15 Minutes) |
| | | | | | | NPO21008 (6 Months) | Terminal Sterilization (121° C. for 15 Minutes) |
| Informed Fluids | APP 114S Film (Polycine) 135 × 0.20 | Polyolefins | 1 | 1963/SM - winged spike port | APP 107 Tubing Ø 6.8 × 8.8 Roll | NPO21001 (6 Months) | Aseptic Filling, Terminal Sterilization (121° C. for 15 Minutes), Terminal Sterilization (115° C. for 20 Minutes) |
| | | | | | | NPO21007 (6 Months) | Aseptic Filling, Terminal Sterilization (121° C. for 15 Minutes) |
| | | | | | | NPO21008 (6 Months) | Terminal Sterilization (121° C. for 15 Minutes) |
| | | | | | | NPO21012 (up to 3 Months) | Terminal Sterilization (121° C. for 15 Minutes) |
| | | | | | | Engineering Batch Lot#21070832 (Initial) | Aseptic Filling, Terminal Sterilization (121° C. for 15 Minutes) |
| Informed Fluids | NEXCEL M312 Film (Sealed Air) 135 × 0.20 | Polyolefins | 1 | 1963/SM - winged spike port | COEX TUBE PP/EVA Ø 6.8 × 8.8 Roll | NPO21012 (up to 3 Months) | Terminal Sterilization (121° C. for 15 Minutes) |
| | | | | | | Engineering Batch Lot#21070832 (Initial) | Aseptic Filling, Terminal Sterilization (121° C. for 15 Minutes) |

Figure 11:
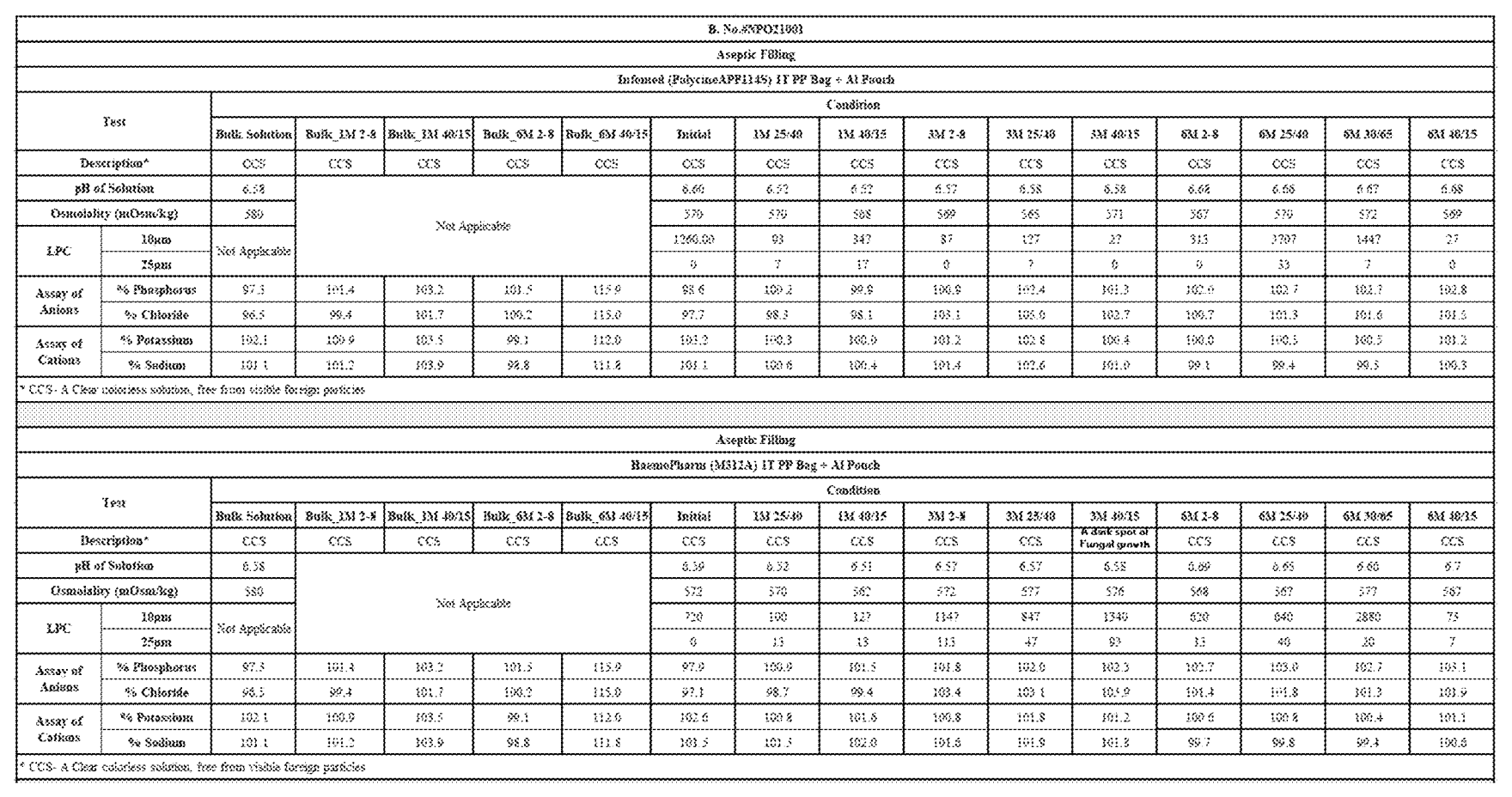
Figure 15:
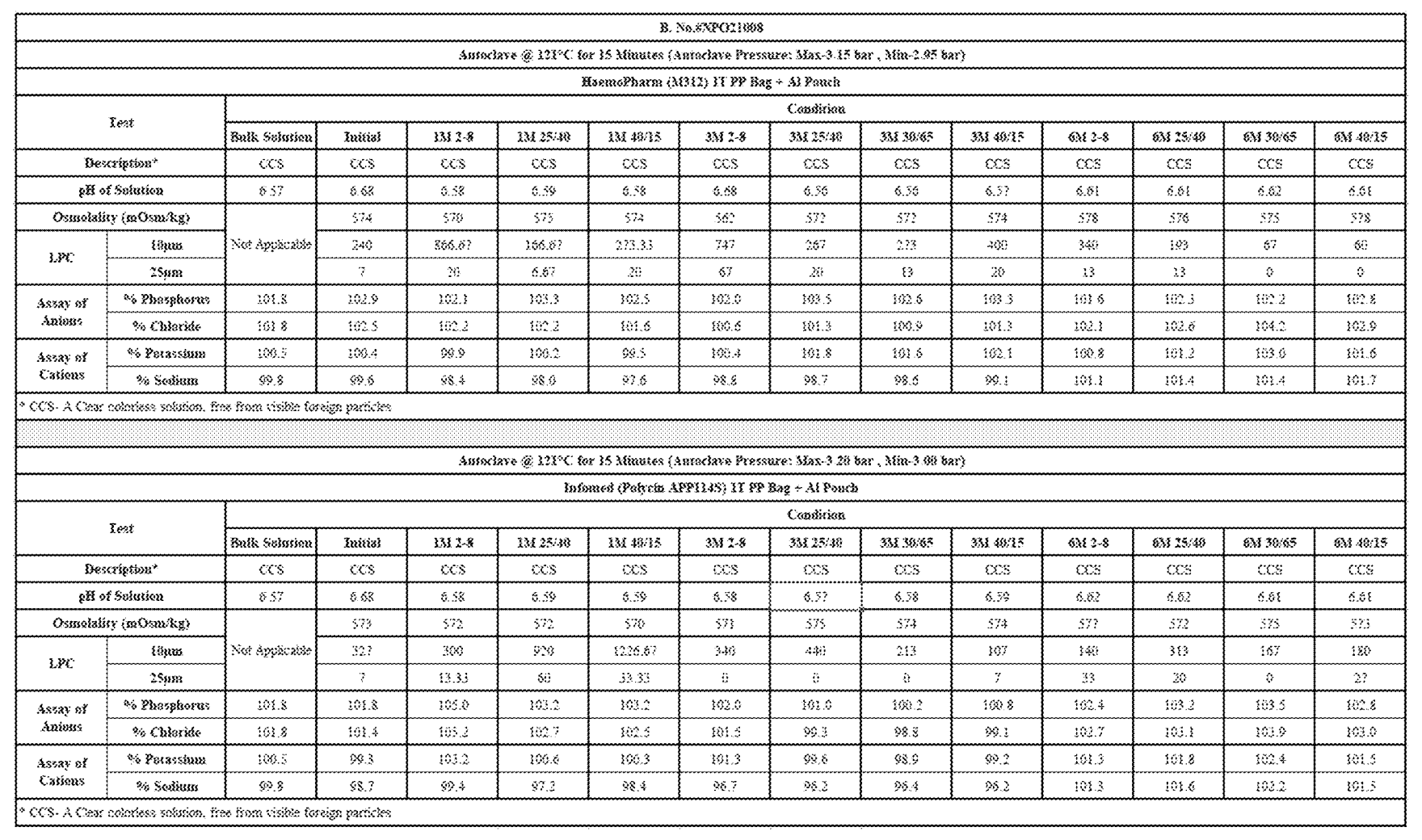
Figure 19:
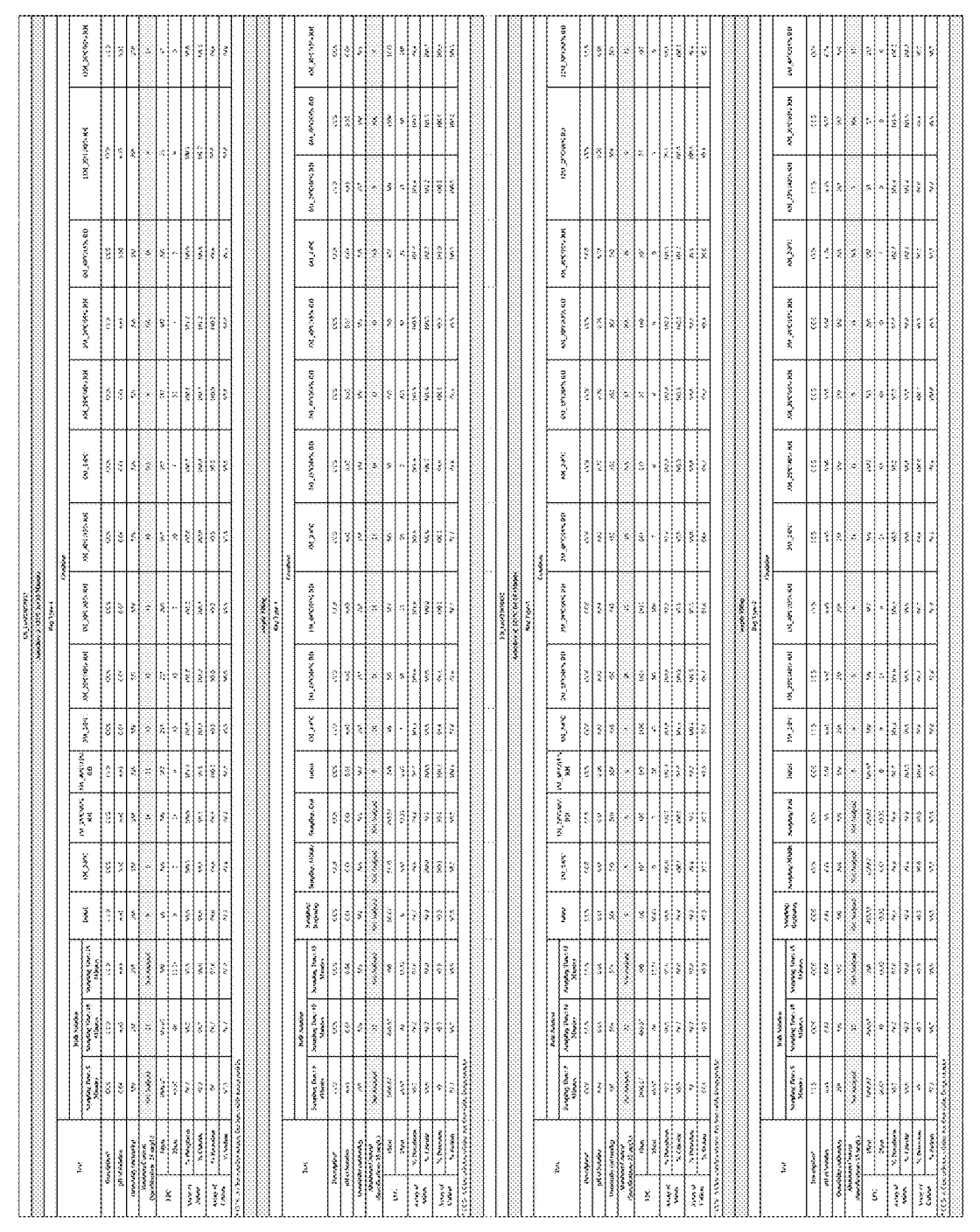

Stability was determined for all samples over various time periods and temperatures as is indicated in the respective "Stability Batches and Results", with detailed results shown in FIGS. 9-17. More specifically, FIG. 9 depicts stability conditions and results for Stability Batch NPO2052, FIG. 10 depicts stability conditions and results for Stability Batch NPO2092, FIG. 11 depicts stability conditions and results for Stability Batch NPO21001, FIG. 12 depicts stability conditions and results for Stability Batch B #192073_11, FIG. 13 depicts stability conditions and results for Stability Batch NPO21006, FIG. 14 depicts stability conditions and results for Stability Batch NPO21007, FIG. 15 depicts stability conditions and results for Stability Batch NPO21008, FIG. 16 depicts stability conditions and results for Stability Batch NPO21012, and FIG. 17 and FIG. 19 depict stability conditions and results for Stability Batch Engineering Batch Lot #21070832. Ingredients for Batch Lot #21070832 (0.15 mmol/mL) were as follows: Monobasic Potassium Phosphate anhydrous (Grade: NF Crystals): 11.2 mg/mL; Dibasic Potassium Phosphate anhydrous (Grade: USP Fine Granular): 11.8 mg/mL; Sodium Chloride (Grade: USP/FCC Granular): 9 mg/mL; water q.s. All formulations listed in FIGS. 9-17 had an aluminum content of less than 50 mcg/L, with most formulations having an aluminum concentration of between about 7-27 mcg/L.

As can be readily seen form the results, the materials of the primary container did exert some influence on storage stability as evidenced by the liquid particle count (LPC) for particle size measurements at 10 and 25 micron. In addition, as can also be seen with certain materials, the presence of an overwrap substantially reduce loss of water via vapor phase as evidenced by the cation and anion concentrations.

In still further experiments, the inventors explored further formulations with phosphorus concentration ranges of between 0.015 and 0.15 mmol/mL. In that regard, it is noted that the molar ratios between the monobasic and dibasic potassium phosphates remained the same as those described above for formulations containing 15 mmol/100 ml phosphorus (0.15 mmol/mL). Moreover, in some embodiments contemplated phosphates solutions included sodium chloride as a tonicity agent at a concentration of about 900 mg/100 mL. However, in other embodiments the concentration of sodium chloride may also be reduced or entirely omitted. In such case, alternate tonicity agents may or may not be included and exemplary alternate agents include glycerol, mannitol, lactose, etc.

For example, in some experiments, the inventors also tested formulations having a ten-fold lower phosphorus concentration, and in particular solutions comprising potassium phosphates and sodium chloride in which the solution comprised 1.5 mmol/100 ml phosphorus (0.015 mmol/mL) and equal or less than 50 mcg/L aluminum. Exemplary stability data for initial formulations and stability date after terminal sterilization for 15 minutes at 121° C. and terminal sterilization for 20 minutes at 121° C. and 15 minutes are shown in FIG. 18. In this context, it is noted that the molar ratio between the monobasic and dibasic potassium phosphates was the same as those described above for formulations containing 15 mmol/100 ml phosphorus (0.15 mmol/mL). Ingredients for NPO2054 (0.015 mmol/mL) were as follows: Monobasic Potassium Phosphate anhydrous (Grade: NF Crystals): 1.12 mg/mL; Dibasic Potassium Phosphate anhydrous (Grade: USP Fine Granular): 1.18 mg/mL; Sodium Chloride (Grade: USP/FCC Granular): 9 mg/mL; water q.s.

Similarly, the inventors prepared additional formulations containing 15 mmol/250 mL phosphates and Table 21 depicts exemplary initial data for these formulations. Tables 22-23 show exemplary stability data for the formulations containing 15 mmol/250 mL. Ingredients for NPO22020, NPO22069A&B, and NPO22070A&B (all 0.06 mmol/mL) were as follows: Monobasic Potassium Phosphate anhydrous (Grade: NF Crystals): 4.48 mg/mL; Dibasic Potassium Phosphate anhydrous (Grade: USP Fine Granular): 4.72 mg/mL; Sodium Chloride (Grade: USP/FCC Granular): 9 mg/mL; water q.s. As can be seen from the data, all tested formulations were exceptionally stable even over extended periods of storage at elevated temperature.

TABLE 21

Potassium Phosphates in Sodium Chloride Injection, Phosphorus 15 mmol/250 mL and Potassium 22 mEq/250 mL
Nexcel M312 1T PP Bag + Al Pouch

| Test | | Specification | Exhibit Batches | | |
|---|---|---|---|---|---|
| | | | B# 68923001 | B# 68923002 | B# 68923003 |
| Description* | | CCS | CCS | CCS | CCS |
| pH of Solution | | 6.0 to 7.0 | 6.6 | 6.6 | 6.60 |
| Osmolality (mOsm/kg) | | 300-500 mOsmol/kg | 399 | 400 | 397 |
| Assay of | % Phosphorus | 90.0% to 110.0% | 99.0 | 98.6 | 98.7 |
| Anions | % Chloride | 90.0% to 110.0% | 100.9 | 99.4 | 100.1 |
| Assay of | % Potassium | 90.0% to 110.0% | 100.3 | 100.5 | 100.4 |
| Cations | % Sodium | 90.0% to 110.0% | 99.7 | 100.7 | 101.5 |
| Aluminum Content (100 µg/L) | | NMT 100 µg/L | 8 | 7 | 18 |

*CCS- A Clear colorless solution, free from visible foreign particles

TABLE 22

B. No. #NPO22069A (15 mmol of Phosphorus/250 mL)
Nexcel M312 1T PP Bag + Al Pouch

| Test | | Specification | Conditions | | |
|---|---|---|---|---|---|
| | | | Initial Autoclaved | 3M 40/15 | 6M 40/15 |
| Description* | | CCS | CCS | CCS | CCS |
| pH of Solution | | 6.0 to 7.0 | 6.73 | 6.65 | 6.59 |
| Osmolality (mOsm/kg) | | 300-500 mOsmol/kg | 433 | 405 | 406 |
| LPC | 10 µm | NMT 25 particles/mL | 8 | 0 | 1 |
| | 25 µm | NMT 3 particles/mL | 0 | 0 | 0 |
| Assay of | % Phosphorus | 90.0% to 110.0% | 98.2 | 101.8 | 99.9 |
| Anions | % Chloride | 90.0% to 110.0% | 98.3 | 103.6 | 98.8 |
| Assay of | % Potassium | 90.0% to 110.0% | 99.0 | 102.6 | 98.3 |
| Cations | % Sodium | 90.0% to 110.0% | 98.3 | 100.8 | 97.1 |
| Aluminum Content (100 µg/L) | | NMT 100 µg/L | 8 | 4 | 5 |

*CCS- A Clear colorless solution, free from visible foreign particles

TABLE 23

B. No. #NPO22070A (15 mmol of Phosphorus/250 mL)
Nexcel M312 1T PP Bag + Al Pouch

| Test | | Specification | Conditions | | | |
|---|---|---|---|---|---|---|
| | | | Initial Autoclaved | 3M 40/15 | In-Use Study_70 days | 6M 40/15 |
| Description* | | CCS | CCS | CCS | CCS | CCS |
| pH of Solution | | 6.0 to 7.0 | 6.72 | 6.63 | 6.65 | 6.60 |
| Osmolality (mOsm/kg) | | 300-500 mOsmol/kg | 433 | 404 | 409 | 407 |
| LPC | 10 µm | NMT 25 particles/mL | 4 | 1 | 0 | 6 |
| | 25 µm | NMT 3 particles/mL | 0 | 0 | 0 | 0 |
| Assay of Anions | % Phosphorus | 90.0% to 110.0% | 97.8 | 99.7 | 98.8 | 100.8 |
| | % Chloride | 90.0% to 110.0% | 98.6 | 103.1 | 103.2 | 100.9 |
| Assay of Cations | % Potassium | 90.0% to 110.0% | 97.0 | 101.2 | 101.1 | 99.3 |
| | % Sodium | 90.0% to 110.0% | 97.9 | 101.0 | 100.9 | 99.5 |
| Aluminum Content (100 µg/L) | | NMT 100 µg/L | 6 | 5 | Not Performed | 2 |

*CCS- A Clear colorless solution, free from visible foreign particles

In yet further experiments, the inventors prepared additional formulations containing 30 mmol/500 mL phosphates, and Tables 24-25 below depict exemplary initial and stability data for such additional formulations. As can be seen, all tested formulations were once more exceptionally stable, even over extended periods of storage at elevated temperature.

TABLE 24

B. No. #NPO22069B (30 mmol of Phosphorus/500 mL)
Nexcel M312 1T PP Bag + Al Pouch

| Test | | Specification | Conditions | | |
|---|---|---|---|---|---|
| | | | Initial Autoclaved | 3M 40/15 | 6M 40/15 |
| Description* | | CCS | CCS | CCS | CCS |
| pH of Solution | | 6.0 to 7.0 | 6.74 | 6.66 | 6.59 |
| Osmolality (mOsm/kg) | | 300-500 mOsmol/kg | 434 | 406 | 405 |
| LPC | 10 µm | NMT 25 particles/mL | 4 | 2 | 21 |
| | 25 µm | NMT 3 particles/mL | 0 | 0 | 1 |
| Assay of Anions | % Phosphorus | 90.0% to 110.0% | 97.4 | 102.0 | 102.4 |
| | % Chloride | 90.0% to 110.0% | 97.8 | 103.9 | 101.6 |
| Assay of Cations | % Potassium | 90.0% to 110.0% | 98.3 | 103.0 | 100.7 |
| | % Sodium | 90.0% to 110.0% | 97.7 | 101.1 | 99.4 |
| Aluminum Content (100 µg/L) | | NMT 100 µg/L | 5 | 4 | 5 |

*CCS- A Clear colorless solution, free from visible foreign particles

TABLE 25

B. No. #NPO22070B (30 mmol of Phosphorus/500 mL)
Nexcel M312 1T PP Bag + Al Pouch

| Test | | Specification | Conditions | | | |
|---|---|---|---|---|---|---|
| | | | Initial Autoclaved | 3M 40/15 | In-Use Study_70 days | 6M 40/15 |
| Description* | | CCS | CCS | CCS | CCS | CCS |
| pH of Solution | | 6.0 to 7.0 | 6.74 | 6.63 | 6.64 | 6.59 |
| Osmolality (mOsm/kg) | | 300-500 mOsmol/kg | 429 | 403 | 408 | 405 |
| LPC | 10 µm | NMT 25 particles/mL | 2 | 3 | 1 | 20 |
| | 25 µm | NMT 3 particles/mL | 0 | 0 | 0 | 0 |
| Assay of Anions | % Phosphorus | 90.0% to 110.0% | 99.0 | 99.5 | 98.4 | 100.7 |
| | % Chloride | 90.0% to 110.0% | 99.1 | 103.0 | 103.1 | 100.8 |
| Assay of Cations | % Potassium | 90.0% to 110.0% | 97.0 | 101.1 | 101.5 | 98.7 |
| | % Sodium | 90.0% to 110.0% | 97.9 | 100.8 | 101.3 | 99.0 |
| Aluminum Content (100 µg/L) | | NMT 100 µg/L | 8 | 3 | Not Performed | 7 |

*CCS- A Clear colorless solution, free from visible foreign particles

In view of the required or recommended rates of infusion and maximum recommended concentrations, it should therefore the appreciated that the formulations presented herein will therefore be not only suitable for administration via central and peripheral lines, but can also be administered without further dilution (and potential attendant calculation errors and risk of contamination). As such, it should also be noted that the formulations presented herein can be provide in volumes suitable for a variety of patents and needs. However, it is especially preferred that the formulations presented herein will be provided in a polymeric bag (preferably a multilayer bag having between 3-7 layers, with a bag typically placed in an overwrap) at volumes of at least 10 mL, and more typically at least 100 mL, and typically no more than 2,000 mL. Therefore, suitable bag volumes will contain 50 mL, 100 mL, 250 mL, 500 mL, or 1,000 mL of contemplated formulations.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sterile ready-to-use aqueous potassium solution, comprising potassium phosphates and sodium chloride, wherein the solution comprises between 1.5 mmol/100 mL and 15 mmol/100 ml phosphorous and equal or less than 50 mcg/L aluminum, and wherein the solution has a pH of between 2 and 6.

2. The solution of claim 1, wherein the potassium phosphates comprise potassium dihydrogen phosphate and potassium hydrogen phosphate at a molar ratio of about 0.7 to 1.3.

3. The solution of claim 2, wherein the potassium dihydrogen phosphate is present in the solution an amount of between about 112 mg/100 ml and about 1,120 mg/100 ml and wherein the potassium hydrogen phosphate is present in the solution in an amount of between about 118 mg/100 ml and about 1,180 mg/100 ml.

4. The solution of claim 1, wherein the potassium is present in the solution in an amount of no more than 22 mEq/100 mL.

5. The solution of claim 1, wherein the sodium chloride is present in the solution in an amount of up to 900 mg/100 ml.

6. The solution of claim 1, wherein the solution has, after autoclaving and storage of at least 3 months at 25° C. and 40% relative humidity, a total liquid particle count of no more than 360 and no more than 30 for particles having a size of equal to or greater than 15 and equal to or greater 25 micrometer size, respectively.

7. The solution of claim 1, wherein the solution has, after autoclaving and storage of at least 3 months at 25° C. and 40% relative humidity, a change in phosphorus of no more than 1% absolute.

8. The solution of claim 1, wherein the solution has, after autoclaving and storage of at least 3 months at 25° C. and 40% relative humidity, a change in potassium of no more than 2% absolute.

9. The solution of claim 1, wherein the solution is packaged in a flexible polyolefin container, optionally at a volume of between 100 mL and 1,000 mL, and optionally wherein the flexible polyolefin container is a flexible multilayer bag.

10. The solution of claim, 9 wherein the flexible polyolefin container is further contained in a secondary metallized overwrap.

11. A sterile ready-to-use premixed pharmaceutical product stored in a flexible polymeric container, wherein the pharmaceutical product comprises a potassium phosphates in an aqueous sodium chloride solution containing (a) less than 50 mcg/L aluminum, (b) between about 1.5 mmol 100 ml and 15 mmol/100 ml phosphorus, and (c) no more than about 22 mEq/100 mL potassium.

12. The pharmaceutical product of claim 11, wherein the potassium phosphates comprise potassium dihydrogen phosphate and potassium hydrogen phosphate at a molar ratio of about 0.7 to 1.3, and/or wherein the potassium dihydrogen phosphate is present in the solution an amount of between about 112 mg/100 ml and about 1,120 mg/100 ml and wherein the potassium hydrogen phosphate is present in the solution in an amount of between about 118 mg/100 ml and about 1,180 mg/100 ml.

13. The pharmaceutical product of claim 12, wherein the sodium chloride is present in the aqueous solution in an amount of up to 900 mg/100 ml.

14. The pharmaceutical product of claim 11, wherein the premixed pharmaceutical product in the flexible polymeric container has a volume of between 100 mL and 1,000 mL.

15. The pharmaceutical product of claim 14, wherein the flexible polyolefin container is a flexible multilayer bag.

16. The pharmaceutical product of claim 11, wherein the flexible polymeric container is enclosed in a secondary metallized overwrap.

17. A method of administering phosphates to a patient in need of phosphorus replacement therapy, comprising: administering, without prior dilution, a sterile, and ready-to-use solution comprising potassium phosphates and sodium chloride solution from a flexible container to the patient at a rate of infusion and by a route of administration corresponding to the patient's age and degree of need of phosphorus replacement; wherein the solution comprises between 1.5 mmol/100 mL and 15 mmol/100 ml phosphorus, no more than about 22 mEq/100 mL potassium, and less than 50 mcg/L aluminum.

18. The method of claim 17, wherein the rate of infusion is 6.8 mmol phosphates per hour or 15 mmol phosphates per hour.

19. The method of claim 17, wherein the route of administration is a central venous catheter or peripheral venous catheter.

20. The method of claim 17, wherein the solution is administered after storage of at least 3 months at 25° C. and 40% relative humidity.

* * * * *

UNITED STATES PATENT AND TRADEMARK OFFICE
CERTIFICATE OF CORRECTION

PATENT NO. : 11,925,661 B2
APPLICATION NO. : 18/460941
DATED : March 12, 2024
INVENTOR(S) : Brijeshkumar B. Pandya et al.

It is certified that error appears in the above-identified patent and that said Letters Patent is hereby corrected as shown below:

In the Claims

Column 30, Line 29, Claim 1:
Change "2 and 6" to "6.2 and 6.8"

Signed and Sealed this
Fourteenth Day of May, 2024

Katherine Kelly Vidal
*Director of the United States Patent and Trademark Office*